(12) United States Patent
Chiang et al.

(10) Patent No.: US 12,714,857 B2
(45) Date of Patent: Aug. 25, 2026

(54) IMPEDANCE-MONITORING METHOD, ELECTRICAL-STIMULATION SYSTEM, AND COMPUTER-READABLE STORAGE MEDIUM

(71) Applicant: GIMER MEDICAL. Co. LTD., New Taipei City (TW)

(72) Inventors: Wan-Ting Chiang, New Taipei City (TW); Jian-Hao Pan, New Taipei City (TW)

(73) Assignee: COFORCE MEDICAL CO., LTD., Taipei City (TW)

( * ) Notice: Subject to any disclaimer, the term of this patent is extended or adjusted under 35 U.S.C. 154(b) by 591 days.

(21) Appl. No.: 17/979,049

(22) Filed: Nov. 2, 2022

(65) Prior Publication Data

US 2023/0201591 A1 Jun. 29, 2023

(30) Foreign Application Priority Data

Dec. 29, 2021 (CN) ........................ 202111637916.4

(51) Int. Cl.
*A61N 1/36* (2006.01)
*A61N 1/05* (2006.01)

(52) U.S. Cl.
CPC ......... *A61N 1/3605* (2013.01); *A61N 1/0551* (2013.01)

(58) Field of Classification Search
CPC .............. A61N 1/36521; A61N 1/3614; A61N 2001/083
See application file for complete search history.

(56) References Cited

U.S. PATENT DOCUMENTS 4,899,750 A 2/1990 Ekwall
5,201,865 A 4/1993 Kuehn
(Continued)

FOREIGN PATENT DOCUMENTS

CN 107096129 A 8/2017
CN 111991695 A 11/2020
CN 113348014 A 9/2021

OTHER PUBLICATIONS

Extended European Search Report for European Application No. 22215614.3, dated May 22, 2023.
(Continued)

*Primary Examiner* — Alyssa M Alter
(74) *Attorney, Agent, or Firm* — Birch, Stewart, Kolasch & Birch, LLP

(57) ABSTRACT

An impedance-monitoring method, applied to an electrical-stimulation device and a lead, is provided. The electrical-stimulation device stores a first impedance value of the electrical-stimulation device and a second impedance value of the lead. The method includes the following steps: utilizing the electrical-stimulation device to generate an electrical-stimulation signal, and to perform electrical stimulation on a target area using the electrical-stimulation signal; utilizing the electrical-stimulation device to sample the electrical-stimulation signal to calculate a total impedance value corresponding to the electrical-stimulation signal; and utilizing the electrical-stimulation device to calculate a tissue-impedance value according to the total impedance value, the first impedance value of the electrical-stimulation device, and the second impedance value of the lead. The tissue-impedance value is used to calculate the energy value of the electrical-stimulation signal transmitted to the target area.

35 Claims, 13 Drawing Sheets

(56) References Cited

U.S. PATENT DOCUMENTS

| | | | | |
|---|---|---|---|---|
| 5,237,991 | A | 8/1993 | Baker, Jr. et al. | |
| 9,101,767 | B2 | 8/2015 | Trier et al. | |
| 9,174,052 | B1 * | 11/2015 | Nabutovsky ....... | A61N 1/36185 |
| 2004/0230245 | A1 | 11/2004 | Prutchi et al. | |
| 2012/0197331 | A1 | 8/2012 | Germanson et al. | |
| 2014/0296941 | A1 | 10/2014 | King et al. | |
| 2015/0306398 | A1 | 10/2015 | Trier et al. | |
| 2020/0353263 | A1 | 11/2020 | Parker et al. | |

OTHER PUBLICATIONS

Swerdlow et al., "Impedance in the Diagnosis of Lead Malfunction", Circulation: Arrhythmia and Electrophysiology, vol. 13, Feb. 2020, pp. 172-186.

Taiwanese Office Action and Search Report for Taiwanese Application No. 111132805, dated Jul. 19, 2023.

Chinese Office Action and Search Report for Chinese Application No. 202111637916.4, dated Mar. 25, 2026.

* cited by examiner

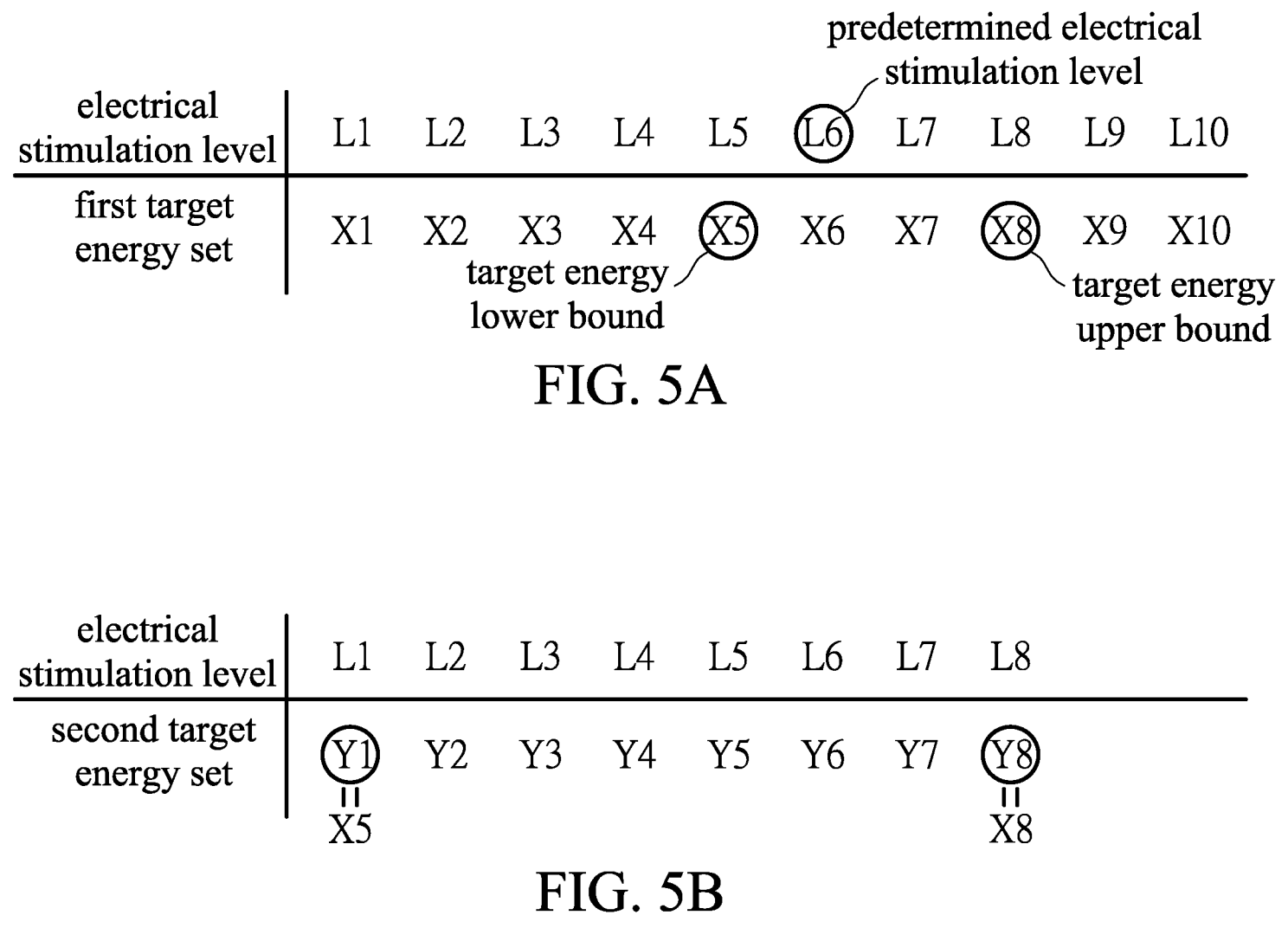

| electrical stimulation level | L1 | L2 | L3 | L4 | L5 | (L6) | L7 | L8 | L9 | L10 |
|---|---|---|---|---|---|---|---|---|---|---|
| first target energy set | X1 | X2 | X3 | X4 | (X5) | X6 | X7 | (X8) | X9 | X10 |

FIG. 5A

| electrical stimulation level | L1 | L2 | L3 | L4 | L5 | L6 | L7 | L8 |
|---|---|---|---|---|---|---|---|---|
| second target energy set | (Y1) = X5 | Y2 | Y3 | Y4 | Y5 | Y6 | Y7 | (Y8) = X8 |

FIG. 5B

IMPEDANCE-MONITORING METHOD, ELECTRICAL-STIMULATION SYSTEM, AND COMPUTER-READABLE STORAGE MEDIUM

CROSS REFERENCE TO RELATED APPLICATIONS

This application claims priority of China Patent Application No. 202111637916.4, filed on Dec. 29, 2021, the entirety of which is incorporated by reference herein.

BACKGROUND

Technology Field

The present disclosure relates in general to electrical-stimulation techniques.

Description of the Related Art

In recent years, dozens of different kinds of therapeutic electrical nerve stimulation devices have been developed, and every year tens of thousands of people undergo surgery to have electrical-stimulation devices implanted. Due to developments in precision manufacturing technology, medical instruments such as implantable electrical-stimulation devices have been shrunk so that they can be implanted into the human body.

After an implantable electrical-stimulation device is implanted into the human body, scar tissue may gradually accumulate on or near the implanted electrical-stimulation device, causing the tissue impedance to change and impacting the electrical-stimulation effect. Therefore, how to effectively monitor the impedance of the tissue is an important topic.

SUMMARY

In view of the problems of the prior art described above, an impedance-monitoring method, an electrical-simulation system, and a computer-readable storage medium are provided in the embodiments of the present disclosure.

An impedance-monitoring method, applied to an electrical-stimulation device and a lead, is provided according to an embodiment of the present disclosure. The electrical-stimulation device stores a first impedance value of the electrical-stimulation device and a second impedance value of the lead. The method includes the following steps: utilizing the electrical-stimulation device to generate an electrical-stimulation signal, and to perform electrical stimulation on a target area using the electrical-stimulation signal; utilizing the electrical-stimulation device to sample the electrical-stimulation signal to calculate a total impedance value corresponding to the electrical-stimulation signal; and utilizing the electrical-stimulation device to calculate a tissue-impedance value according to the total impedance value, the first impedance value of the electrical-stimulation device, and the second impedance value of the lead, wherein the tissue-impedance value is used to calculate an energy value of the electrical-stimulation signal transmitted to the target area.

An electrical-stimulation system is provided according to an embodiment of the present disclosure. The electrical-stimulation system includes: an external control device, a lead, and an electrical-stimulation device. The electrical-stimulation device is electrically connected to the external device and the lead. The electrical-stimulation device includes a storage unit, an electrical-stimulation-signal generating circuit, a sampling module, and a calculation module. The storage unit stores a first impedance value of the electrical-stimulation device and a second impedance value of the lead. The electrical-stimulation-signal generating circuit generates an electrical-stimulation signal and performing electrical stimulation on a target area using the electrical-stimulation signal. The sampling module samples the electrical-stimulation signal. The calculation module calculates a tissue-impedance value according to the total impedance value, the first impedance value of the electrical-stimulation device, and the second impedance value of the lead. The tissue-impedance value is used to calculate an energy value of the electrical-stimulation signal transmitted to the target area.

An external control device is provided according to an embodiment of the present disclosure. The external control device is applied.

A computer-readable storage medium is provided according to an embodiment of the present disclosure. The computer-readable storage medium stores one or more instructions, and cooperates with an electrical-stimulation device and an external control device. When the instructions are executed by the electrical-stimulation device, the electrical-stimulation device and the external control device execute the following operations: utilizing the electrical-stimulation device to generate an electrical-stimulation signal, and to perform electrical stimulation on a target area using the electrical-stimulation signal; utilizing the electrical-stimulation device to sample the electrical-stimulation signal to calculate a total impedance value corresponding to the electrical-stimulation signal; and utilizing the electrical-stimulation device to calculate a tissue-impedance value according to the total impedance value, the first impedance value of the electrical-stimulation device, and the second impedance value of the lead, wherein the tissue-impedance value is used to calculate an energy value of the electrical-stimulation signal transmitted to the target area.

It will be apparent to those skilled in the art that various modifications and variations can be made in the present disclosure, without departing from the spirit and scope of the present disclosure.

BRIEF DESCRIPTION OF THE DRAWINGS

The present disclosure can be more fully understood by reading the subsequent detailed description and examples with references made to the accompanying drawings, wherein:

FIG. 5A illustrates the first target energy set in accordance with an embodiment of the present disclosure;

FIG. 5B illustrates the second target energy set in accordance with to another embodiment of the present disclosure;

DETAILED DESCRIPTION OF THE INVENTION

The following description is a preferred embodiment of the invention, which is intended to describe the basic spirit of the invention, but is not intended to limit the invention. For the actual inventive content, reference must be made to the scope of the claims.

Figure 1:
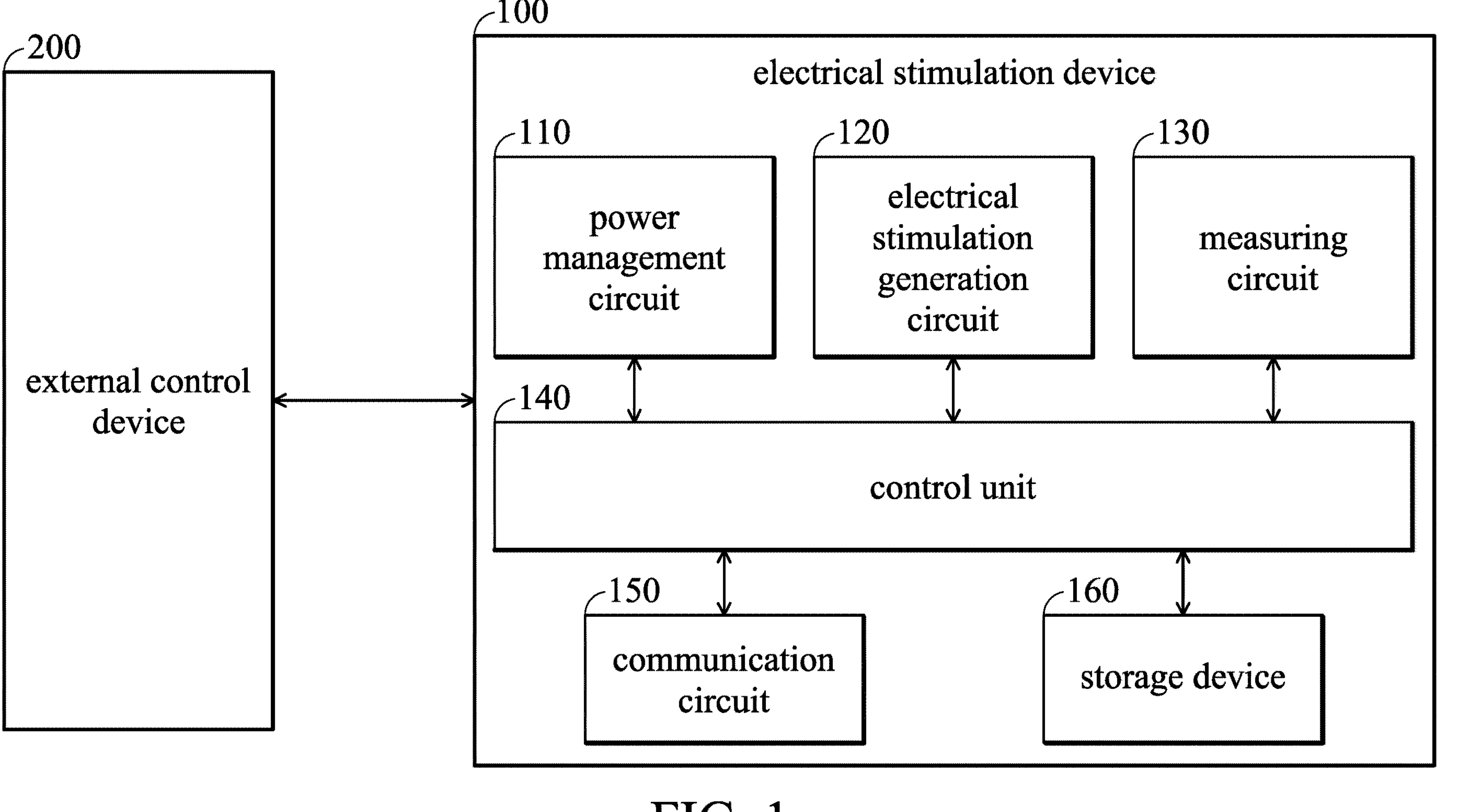
FIG. 1 is a block diagram of an electrical-stimulation device in accordance with an embodiment of the present disclosure.

FIG. 1 is a block diagram of an electrical-stimulation device 100 in accordance with an embodiment of the present disclosure. As shown in FIG. 1, the electrical-stimulation device 100 at least includes a power management circuit 110, an electrical-stimulation generation circuit 120, a measuring circuit 130, a control unit 140, a communication circuit 150, and a storage unit 160. It should be noted that the block diagram shown in FIG. 1 is only for the convenience of explaining the embodiments of the present disclosure, the present disclosure is not limited thereto. The electrical-stimulation device 100 may also include other elements.

According to an embodiment of the present disclosure, the electrical-stimulation device 100 may be electrically coupled to an external control device 200. The external control device 200 may be provided with an operation interface. According to user's operation on the operation interface, the external control device 200 may generate instructions or signals to be transmitted to the electrical-stimulation device 100, and transmits the instructions or signals to the electrical-stimulation device 100 via a wire communication (e.g., a transmission line).

In addition, in accordance with another embodiment of the present disclosure, the external control device 200 may transmit the instructions or signals to the electrical-stimulation device 100 via a wireless communication, such as Bluetooth, Wi-Fi, or NFC (near-field communication).

According to the embodiment of the present disclosure, the electrical-stimulation device 100 may be an implantable electrical-stimulation device, an external electrical-stimulation device with a lead implanted into human body, or a transcutaneous electrical-stimulation device (TENS). According to an embodiment of the present disclosure, when the electrical-stimulation device 100 is a non-implantable electrical-stimulation device (e.g., an external electrical-stimulation device or a transcutaneous electrical-stimulation device), the electrical-stimulation device 100 may be integrated with the external control device into a device. According to an embodiment of the present disclosure, the electrical-stimulation device 100 may be an electrical-stimulation device with batteries, or an electrical-stimulation device of which power is transmitted wirelessly by the external control device 200. According to an embodiment of the present disclosure, in a trial phase, the electrical-stimulation device 100 is an external electrical-stimulation device with a lead implanted into human body. There are electrodes on the lead, so that the external electrical-stimulation device may send the electrical-stimulation signal to the corresponding target area via the electrodes on the lead. In the trial phase, after the terminal of the lead with an electrode has been implanted into the human body, the other terminal is thereby linked to the external control device 200, and the external stimulation device may send an electrical-stimulation signal to evaluate the effectiveness of the therapy, and to confirm whether the functions of the lead are normal, and whether the position into which the lead is implanted is correct. In the trial phase, the external control device 200 may first pair with the external electrical-stimulation device (i.e., a non-implantable electrical-stimulation device). After the lead is implanted into the human body, the external electrical-stimulation device may be connected to the lead. The external electrical-stimulation device may be wirelessly controlled by the external control device 200 to perform electrical-stimulation of the human body. According to an embodiment of the present disclosure, if the evaluation in the trial phase is effective, a permanent implantation phase may be entered. In the permanent implantation phase, the electrical-stimulation device 100 is implanted into the human body together with the lead. The electrical-stimulation device 100 sends the electrical signal to the corresponding target area via the electrodes on the lead. While the external control device 200 is entering the permanent implantation phase, a user or a doctor must let the external control device 200 detect a phase change card, so as to change the state of the external control device 200 from the trial phase to the permanent implantation phase via near-field wireless communication. In addition, the external control device 200 may select a target energy upper bound and a target energy lower bound from the first target energy set according to a predetermined electrical-stimulation level. Then, the external control device 200 may generate the second target energy set according to the target energy upper bound and the target energy lower bound (further explanation will be provided). Moreover, before the permanent implantation phase or during the permanent implantation phase, the external control device 200 may pair with the implantable electrical-stimulation device first, and the external electrical-stimulation device (i.e., a non-implantable electrical-stimulation device) may be removed, and the electrical-stimulation device 100 (i.e., an implantable electrical-stimulation device) connects to the lead and is implanted into the human body.

According to the embodiment of the present disclosure, the power management circuit 110 is used for providing power to the elements and circuit in the electrical-stimulation device 100. The power provided by the power management circuit 110 may be from a built-in rechargeable battery, or the external control device 200, but the present disclosure is not limited thereto. The external control device 200 may provide power to the power management circuit 110 using a wireless power technology. The power management circuit 110 may be activated or deactivated according to the instructions of the external control device 200. According to an embodiment of the present disclosure, the power management circuit 110 may include a switch circuit (not shown in the figure). The switch circuit may be switched on or off according to the instructions of the external control device 200, so as to activate or deactivate the power management circuit 110.

According to the embodiment of the present disclosure, the electrical-stimulation signal generation circuit 120 is used for generating the electrical-stimulation signal. The electrical-stimulation device 100 may transmit the generated electrical-stimulation signal to the electrodes via at least a lead, so as to perform electrical-stimulation on the target area of the body of a user (human or animal) or a patient. The target area may be, for example, spine, spinal nerve, dorsal root ganglia, cranial nerve, vagus nerve, trigeminal nerve, lateral recess, or peripheral nerve, but the present disclosure is not limited thereto. A detailed illustration of the structure of the electrical-stimulation signal generation circuit 120 is provided in FIG. 4.

Figure 2A:
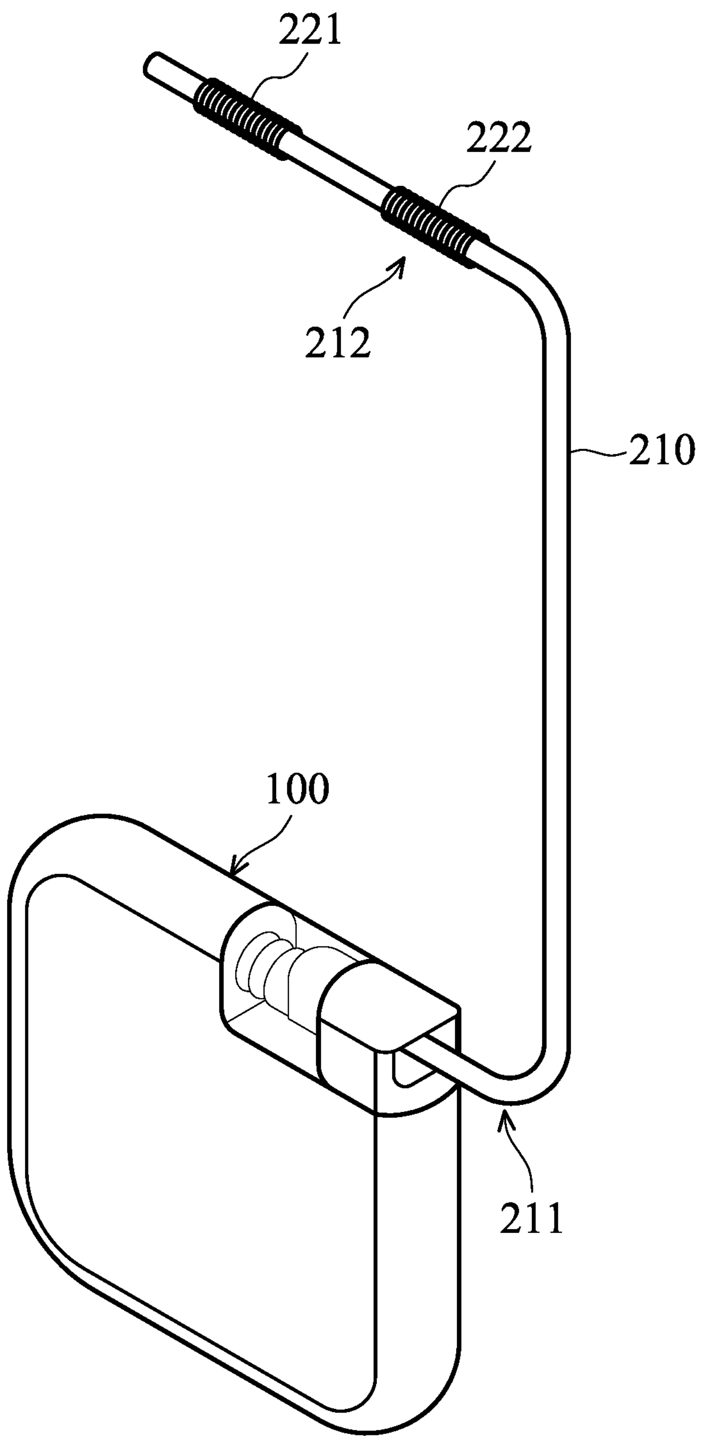
FIG. 2A is a schematic diagram of an electrical-stimulation device in accordance with an embodiment of the present disclosure.

FIG. 2A is the schematic diagram of an electrical-stimulation device 100 in accordance with an embodiment of the present disclosure. As shown in FIG. 2A, the electrical-stimulation signal may be output to the lead 210, so that the electrical-stimulation signal may be transmitted via a terminal 211 of the lead 210 to the other terminal 212 (e.g., electrode 221 or 222) of the lead 210 to perform electrical-simulation operations on the target area. In an embodiment of the present disclosure, the electrical-stimulation device 100 and the lead 210 may be separately electrically connected to each other, but the present disclosure is not limited thereto. For example, the electrical-stimulation device 100 and the lead 210 may be a monolithic device.

Figure 2B:
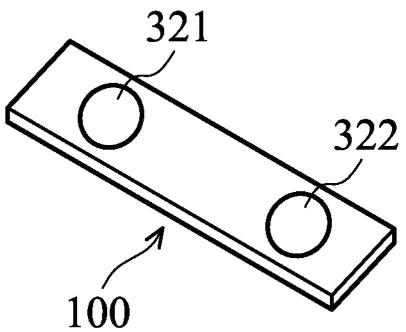
FIG. 2B is a schematic diagram of an electrical-stimulation device in accordance with another embodiment of the present disclosure.

FIG. 2B is the schematic diagram of an electrical-stimulation device 100 in accordance with another embodiment of the present disclosure. As shown in FIG. 2B, the electrode 321 and the electrode 322 may be directly installed on one side of the electrical-stimulation device 100. The electrical-stimulation signal may be transmitted to the electrode 321 or the electrode 322, so as to perform electrical-stimulation on the target area. In other words, in this embodiment, the electrical-stimulation device 100 does not need to transmit the electrical-stimulation signal to the electrode 321 and the electrode 322 via the lead.

Figure 3:
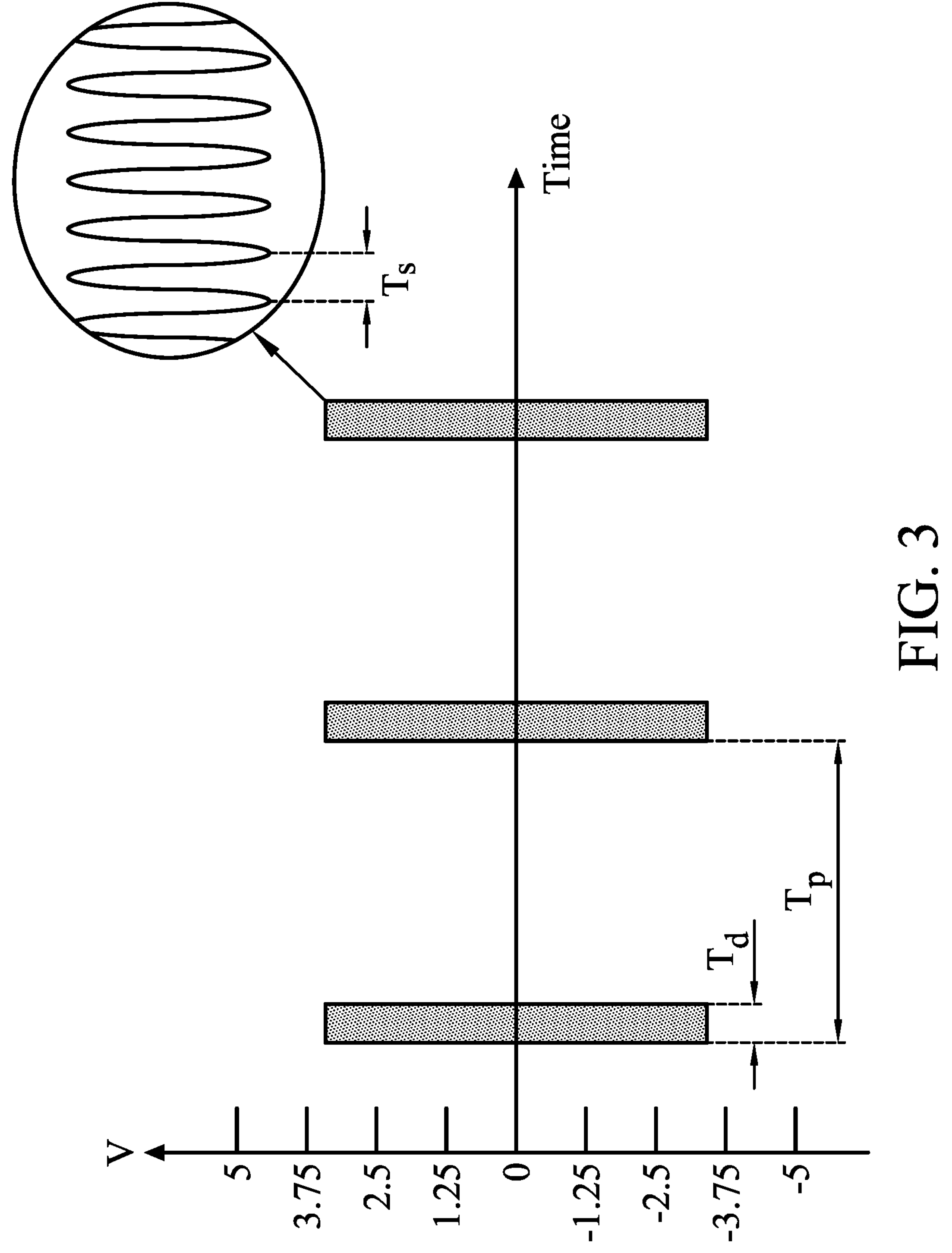
FIG. 3 is a waveform diagram of the electrical-stimulation signals of the electrical-stimulation device in accordance with an embodiment of the present disclosure.

FIG. 3 is the waveform diagram of the electrical-stimulation signals of the electrical-stimulation device in accordance with an embodiment of the present disclosure. As shown in FIG. 3 in accordance with an embodiment of the present disclosure, the electrical-stimulation signal may be a pulsed radio-frequency (PRF) signal (also referred to as a pulse signal, for short), a continuous sinusoidal waveform, or a continuous triangle waveform, but the present disclosure is not limited thereto. Besides, when the electrical-stimulation signal is a pulse AC (alternating current) signal, a pulse cycle time $T_p$ includes a pulse signal and at least an idle period, and the pulse cycle time $T_p$ is the inverse of the pulse repetition frequency. For example, the pulse repetition frequency (also referred to as the pulse frequency, for short) may ranges from 0 Hertz to 1K Hertz, preferably range from 1 Hertz to 100 Hertz. In this embodiment, the exemplary pulse repetition frequency of the electrical-stimulation signal is 2 Hertz. Besides, the duration time $T_d$ (i.e., the pulse width) of a pulse in a pulse cycle time may be at 1-250 milliseconds, preferably at 10-100 milliseconds. In this embodiment, the exemplary duration time $T_d$ is 25 milliseconds. In this embodiment, the frequency of the electrical-stimulation signal is 500K Hertz. In other words, the electrical-stimulation signal cycle time $T_s$ is approximately 2 microseconds(μs). In addition, the frequency of the electrical-stimulation signal is the intra-pulse frequency in each pulse AC signal of FIG. 3. In some embodiments, the intra-pulse frequency of the electrical-stimulation signal may, for example, range from 1K Hertz to 1000K Hertz. It should be appreciated that in each embodiment of the present disclosure, the frequency of the electrical-stimulation signal refers to the intra-pulse frequency of the electrical-stimulation signal. Furthermore, the intra-pulse frequency of the electrical-stimulation signal may, for example, range from 200K Hertz to 800K Hertz. Furthermore, the intra-pulse frequency of the electrical-stimulation signal may, for example, range from 480K Hertz to 520K Hertz. Furthermore, the intra-pulse frequency of the electrical-stimulation signal may be, for example, 500K Hertz. The voltage of the electrical-stimulation signal may range from −25V~+25V. Furthermore, the voltage of the electrical-stimulation signal may range from −20V~+20V. The current of the electrical-stimulation signal may range from 0~60 mA. Furthermore, the current of the electrical-stimulation signal may range from 0~50 mA.

According to an embodiment of the present disclosure, a user may operate the electrical-stimulation device 100 to perform electrical-stimulation only when in need (e.g., the symptom becomes more serious or does not alleviate). After the electrical-stimulation device 100 has performed electrical-stimulation on the target area once, the electrical-stimulation device 100 must wait for a limited period before performing electrical-stimulation on the target area again. For example, after the electrical-stimulation device 100 has performed electrical-stimulation on the target area once, the electrical-stimulation device 100 must wait for 30 minutes (i.e., the limited period) before performing electrical-stimulation on the target area again, but the present disclosure is not limited thereto. The limited period may be 45 minutes, 1 hour, 4 hours, or any time period within 24 hours.

According to the embodiment of the present disclosure, the measuring circuit 130 may measure the voltage value and the current value of the electrical-stimulation signal according to the electrical-stimulation signal generated by the electrical-stimulation signal generation circuit 120. In addition, the measuring circuit 130 may measure the voltage value and the current value on the tissues in the target area of the body of the user or the patient. According to an embodiment of the present disclosure, the measuring circuit 130 may adjust the current and the voltage of the electrical-stimulation signal according to the instructions of the control unit 140. A detailed illustration of the structure of the measuring circuit 130 is provided in FIG. 4.

According to the embodiment of the present disclosure, the control unit 140 may be a controller, a microcontroller, or a processor, but the present disclosure is not limited thereto. The control unit 140 may be used for controlling the electrical-stimulation signal generation circuit 120 and the measuring circuit 130. The operations regarding the control unit 140 will be explained in FIG. 4.

According to the embodiment of the present disclosure, the communication circuit 150 may be used for communicating with the external control device 200. The communication circuit 150 may transmit the instructions or signals received by the external control device 200 to the control unit 140, and transmit the data measured by the electrical-stimulation device 100 to the external control device 200. According to the embodiment of the present disclosure, the communication circuit 150 may be a wireless communication or a wire communication for communicating with the external control device 200.

According to an embodiment of the present disclosure, all the electrodes of the electrical-stimulation device 100 may be activated during the electrical-stimulation. Therefore, users do not need to select which electrodes on the lead to be activated, and do not need to select which activated electrodes are negative polarity or positive polarity. For example, if the electrical-stimulation device 100 is equipped with 8 electrodes, these 8 electrodes can be 4 positive polarities and 4 negative polarities staggeringly arranged.

A pulse signal that is lower (e.g., 10K Hertz) than conventional electrical-stimulation may be prone to cause discomfort such as the feeling of stabbing pain, or paresthesia to the user. In an embodiment of the present disclosure, the electrical-stimulation signal is a high frequency (e.g., 500K Hertz) pulse signal, so it will not cause paresthesia to users, or just cause extremely slight paresthesia to users.

According to the embodiment of the present disclosure, the storage unit 160 may be a volatile memory (e.g., a random access memory (RAM)), or a non-volatile memory (e.g., flash memory), a read-only memory (ROM), a hard disk drive (HDD), or any combination thereof. The storage unit 160 may be used for storing the files and data required for performing the electrical-stimulation. According to an embodiment of the present disclosure, the storage unit 160 may be used for storing related information of the lookup table provided by the external control device 200.

Figure 4:
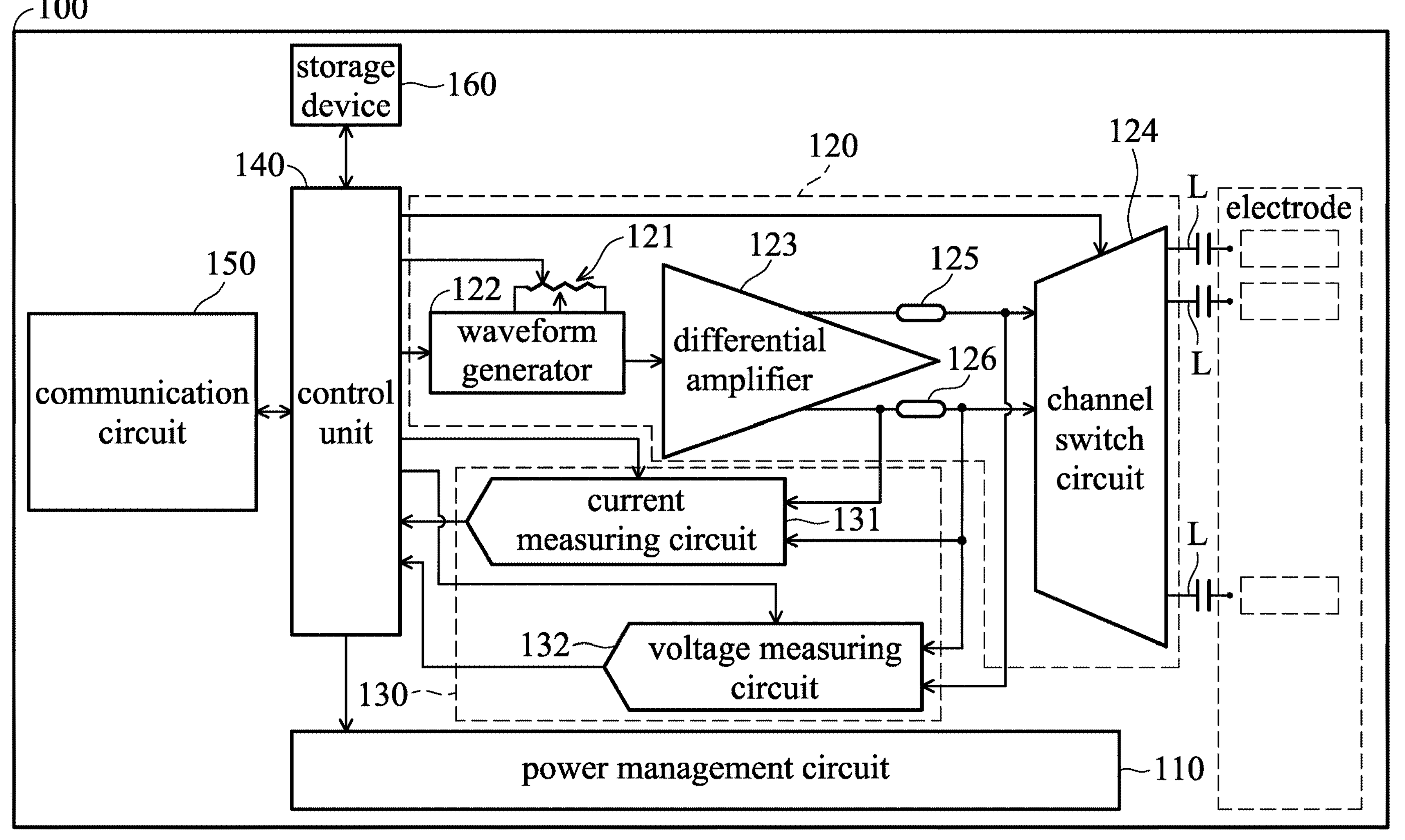
FIG. 4 is a detailed schematic diagram of an electrical-stimulation device in accordance with an embodiment of the present disclosure.

FIG. 4 is a schematic diagram of an electrical-stimulation device 100 in accordance with an embodiment of the present disclosure. As shown in FIG. 4, the electrical-stimulation signal generation circuit 120 may include a variable resistor 121, a waveform generator 122, a differential amplifier 123, a channel-switch circuit 124, a first resistor 125, and a second resistor 126. The measuring circuit 130 may include a current-measuring circuit 131 and a voltage-measuring circuit 132. It should be noted that the schematic diagram shown in FIG. 4 is only for the convenience to explain the embodiments of the present disclosure, but the present disclosure is not limited to FIG. 4. The electrical-stimulation device 400 may also include other elements, or other equivalent circuits.

As shown in FIG. 4, according to the embodiment of the present disclosure, the variable resistor 121 may be coupled to a serial peripheral interface (SPI) (not shown in the figure) of the control unit 140. The control unit 140 may transmit instructions to the variable resistor 121 via the SPI to adjust the resistance of the resistor 121, so as to adjust the amplitude of the electrical-stimulation signal to be output. The waveform generator 122 may be coupled to a pulse-width-modulation (PWM) signal generator (not shown in the figure) of the control unit 140. The PWM signal generator may generate a square wave signal, and transmit the square wave signal to the waveform generator 122. After receiving the square wave signal generated by the PWM signal generator, the waveform generator 122 will convert the square wave signal into a sinusoidal wave signal, and transmit the sinusoidal wave signal to the differential amplifier 123. The differential amplifier 123 may convert the sinusoidal wave signal into a differential signal (i.e., the electrical-stimulation signal output), and transmit the differential signal to the channel switch circuit 124 via the first resistor 125 and the second resistor 126. The channel switch circuit 124 may transmit the differential signal (i.e., the output electrical-stimulation signal) to the electrode corresponding to each channel via the lead L in turn according to the instructions of the control unit 140.

As shown in FIG. 4, according to the embodiment of the present disclosure, the current-measuring circuit 131 and the voltage-measuring circuit 132 may be coupled to the differential amplifier 123, so as to obtain the current value and the voltage value of the differential signal (i.e., the electrical-stimulation signal output). Besides, the current-measuring circuit 131 and the voltage-measuring circuit 132 may be used for measuring the voltage value and the current value on the tissues in the target area of the body of the user or the patient. In addition, the current-measuring circuit 131 and the voltage-measuring circuit 132 may be coupled to the input/output (I/O) interface (not shown in the figure) of the control unit 140, so as to receive the instructions from the control unit 140. According to the instructions of the control unit 140, the current-measuring circuit 131 and the voltage-measuring circuit 132 may adjust the current and the voltage of the electrical-stimulation signal until they are a current value and a voltage value that are suitable for the control unit 140. For example, if the voltage value measured by the voltage-measuring circuit 132 is ±10V, and the control unit 140 is suitable for processing a voltage value of 0~3 Volts, then the voltage-measuring circuit 132 may decrease the voltage value to ±1.5V, and then increase the voltage value to 0~3V.

After adjusting the current value and the voltage value, the current-measuring circuit 131 and the voltage-measuring circuit 132 may transmit the adjusted electrical-stimulation signal to the analog-to-digital convertor (ADC) (not shown in the figure) of the control unit 140. The ADC may take samples from the electrical-stimulation signal for the control unit to perform subsequent computation and analysis.

According to an embodiment of the present disclosure, when performing electrical-stimulation on the target area of the body of a patient, the user (medical personnel or the patient himself) may select an electrical-stimulation level from among a plurality of electrical-stimulation levels on the operation interface of the external control device 200. In the embodiment of the present disclosure, different electrical-stimulation levels may correspond to different target energies. The target energy may be a set of default energy. When the user selects an electrical-stimulation level, the electrical-stimulation device 100 may find out how many millijoules of energy must be provided to the target area in order to perform the electrical-stimulation, according to the target energy corresponding to the electrical-stimulation level selected by the doctor or the user. According to the embodiment of the present disclosure, in the trial phase, a plurality of target energies corresponding to a plurality of electrical-stimulation levels may be regarded as a first set of default target energy. According to the embodiment of the present disclosure, the first set of the default target energy (i.e., the target energies) may be a linear sequence, an arithmetic sequence, or a geometric sequence, but the present disclosure is not limited thereto.

According to an embodiment of the present disclosure, in the trial phase, the external control device 200 may be provided with a first lookup table. In this embodiment, the first lookup table may record each of the electrical-stimulation levels and the corresponding target energy. Therefore, according to the electrical-stimulation level selected by the user, the external control device 200 may look up the first lookup table, and obtain the target energy corresponding to the electrical-stimulation level selected by the user from the first target energy set. After obtaining the target energy corresponding to the electrical-stimulation level selected by the user, the external control device 200 will transmit the target energy to the electrical-stimulation device 100. Thus, the electrical-stimulation device 100 may perform electrical-stimulation on the target area according to the target energy.

According to another embodiment of the present disclosure, the electrical-stimulation device 100 may be provided with a built-in first lookup table (e.g., a first lookup table stored in the storage unit 160). In this embodiment, the first lookup table may record each of the electrical-stimulation levels and the corresponding target energy. After the user has selected an electrical-stimulation level from the external control device, the external control device 200 will transmit an instruction to inform the control unit 140 of the electrical-stimulation device 100 which electrical-stimulation level was selected by the user. Then, the control unit 140 may select the target energy that corresponds to the electrical-stimulation level selected by the user from the first target energy set according to the built-in first lookup table. After obtaining the target energy, the electrical-stimulation device 100 may perform electrical-stimulation on the target area according to the selected target energy, until the corresponding first target energy is transmitted to the target area and the time for the electrical-stimulation ends. One round of electrical stimulation is thus completed.

According to another embodiment of the present disclosure, the communication circuit 150 may first obtain the electrical-stimulation level selected by the user, and the first lookup table, from the external control device 200. In this embodiment, the first lookup table may record the electrical-stimulation level and the corresponding target energy. Then, the control unit 140 selects the target energy that corresponds to the electrical-stimulation level selected by the user from the first target energy set, according to the electrical-stimulation level selected by the user and the first lookup table that are obtained from the external control device 200. After obtaining the target energy, the electrical-stimulation device 100 may thus perform electrical stimulation on the target area according to the target energy.

According to the embodiment of the present disclosure, the users may select the electrical-stimulation level from the lowest level (the lowest level of electrical stimulation corresponds to the lowest target energy in the first target energy set). After the electrical stimulation ends and the limited period passes, the next target energy may be selected from the first target energy set. Once the user finds the target energy that he/she prefers or that is more therapeutically effective, then the target energy may be regarded as a predetermined target energy, and the electrical-stimulation level corresponding to the predetermined target energy may be regarded as a predetermined electrical-stimulation level.

According to an embodiment of the present disclosure, in the permanent implantation phase, the external control device 200 (e.g., a controller of the external control device 200) may select a target energy upper bound and a target energy lower bound from the first target energy set according to the predetermined electrical-stimulation level. Then, the external control device 200 (e.g., a controller of the external control device 200) may generate a second target energy set according to the target energy upper bound and the target energy lower bound. In this embodiment, the external control device 200 (e.g., a controller of the external control device 200) may generate a second lookup table according to the electrical-stimulation level corresponding to each of the target energies in the second target energy set. The external control device 200 may transmit the second lookup table and the related parameter information to the electrical-stimulation device 100. When the user is operating the external control device 200, the electrical-stimulation device 100 may perform electrical stimulation according to the second lookup table and the related parameter information. According to an embodiment of the present disclosure, in the trial phase, an external electrical-stimulation device (i.e., a non-implantable electrical-stimulation device) is used to perform electrical stimulation according to the first target energy set in the first lookup table selected by the user. In the permanent phase, the electrical-stimulation device 100 (i.e., an implantable electrical-stimulation device) is used to perform electrical stimulation according to the second target energy set in the second lookup table selected by the user. In an embodiment of the present disclosure, the electrical-stimulation device 100 performs electrical stimulation on the target area until the corresponding second target energy is transmitted to the target area, and this round of electrical stimulation ends. One round of electrical stimulation is thus completed.

According to another embodiment of the present disclosure, in the permanent implantation phase, the electrical-stimulation device 100 may select a target energy upper bound and a target energy lower bound from the first target energy set according to the predetermined electrical-stimulation level. Then, the electrical-stimulation device 100 may generate the second target energy set according to the target energy upper bound and the target energy lower bound. In this embodiment, the electrical-stimulation device 100 may generate a second lookup table according to the second target energy set and the electrical-stimulation level corresponding to each of the target energies in the second target energy set. The electrical-stimulation device 100 may transmit the second lookup table and the related parameter information to the external control device 200. When the user is operating the external control device 200, the electrical-stimulation device 100 may perform electrical stimulation according to the second lookup table and the related parameter information.

According to the embodiment of the present disclosure, the second target energy set may be a linear sequence, an arithmetic sequence, or a geometric sequence, but the present disclosure is not limited thereto. According to an embodiment of the present disclosure, the number of the target energies included by the first target energy set may be the same as the number of the target energies included by the second target energy set. According to another embodiment of the present disclosure, the number of the target energies included by the first target energy set may be different to the number of the target energies included by the second target energy set.

FIG. 5A illustrates the first target energy set in accordance with an embodiment of the present disclosure. FIG. 5B illustrates the second target energy set in accordance with an embodiment of the present disclosure. It should be noted that FIG. 5A and FIG. 5B are only for depicting an embodiment of the present disclosure, but the present disclosure is not limited to the first target energy set and the second target energy set in FIG. 5A and FIG. 5B.

As shown in FIG. 5A, the first lookup table may store the correspondence between electrical-stimulation levels and the first target energies. The first target energy set may include the target energy X1-X10. The electrical-stimulation level Level 1(L1)-Level 10(L10) correspond to the target energies X1-X10 respectively, and the unit of the target energy is millijoule. In addition to the target energies, the electrical-stimulation levels L1-L10 may further correspond to different current values or voltage values. In this embodiment, in the trial phase, when the predetermined electrical-stimulation level selected by the user is L6 (the corresponding predetermined target energy is X6), the predefined target energy upper bound is X8 and the target energy lower bound is X5. There is a target energy between the target energy upper bound X8 and the predetermined target energy X6, while there is no target energy between the target energy lower bound X5 and the predetermined target energy X6.

In the permanent implantation phase, after obtaining the target energy upper bound X8 and the target energy lower bound X5, the electrical-stimulation device 100 or the external control device 200 may generate the second target energy set according to the target energy upper bound X8 and the target energy lower bound X5. As shown in FIG. 5B, the second target energy set may include target energies Y1-Y8, which correspond to the electrical-stimulation levels L1-L8 of the external control device 200 respectively. Besides, in this embodiment, the lowest target energy Y1 of the second target energy set corresponds to the target energy lower bound X5, and the highest target energy Y8 corresponds to the target energy upper bound X8. In the permanent implantation phase, the electrical-stimulation device 100 and the external control device 200 may perform operations of electrical stimulation according to the second target energy set.

According to the embodiment of the present disclosure, when corresponding to a predetermined electrical-stimulation level in the trial phase, the first target energy set may include a target energy upper bound and a target energy lower bound. The target energy upper bound and the target energy lower bound will be brought into the permanent implantation phase. The target energy upper bound will be the highest target energy in the second target energy set, and the target energy lower bound will be the lowest target energy in the second target energy set (as shown in FIG. 5B). As such, the user may perform the electrical-stimulation in the permanent implantation phase using an energy intensity near the predetermined electrical-stimulation level selected, thus the safety of the electrical-stimulation is further assured.

According to an embodiment of the present disclosure, there is a first number of target energies between the target energy upper bound and the predetermined target energy, and there is a second number of target energies between the target energy lower bound and the predetermined target energy. According to an embodiment of the present disclosure, the first number (e.g., 2) is larger than the second number (e.g., 1) (as shown in FIG. 5A). According to another embodiment of the present disclosure, the first number may be equivalent to the second number.

According to an embodiment of the present disclosure, the predetermined target energy is not included in the second target energy set (as shown in FIG. 5B). According to another embodiment of the present disclosure, the predetermined target energy may be included in the second target energy set.

According to an embodiment of the present disclosure, the trial phase and the permanent implantation phase may both be further divided into a non-electrically stimulating phase and an electrically stimulating phase. In other words, the trial phase may include the non-electrically stimulating phase and the electrically stimulating phase, and the permanent implantation phase may also include the non-electrically stimulating phase and the electrically stimulating phase. The non-electrically stimulating phase refers to the synchronization procedure when the electrical-stimulation device 100 and the external control device 200 have just been turned on, or after the electrical-stimulation device 100 and the external control device 200 have been connected, but the user has not yet initiated electrical stimulation. The electrically stimulating phase refers to the course when the electrical-stimulation device 100 has started providing electrical-stimulation treatment. It should be noted that the method of how to calculate the tissue impedance value is applicable to the trial phase or the permanent implantation phase.

According to an embodiment of the present disclosure, when the electrical-stimulation device 100 performs electrical stimulation on the target area, the control unit 140 of the electrical-stimulation device 100 may determine whether the signal quality of the electrical-stimulation signal generated by the electrical-stimulation signal-generating circuit 120 meets a threshold criterion. There will be more details description in the following sections.

Figure 6:
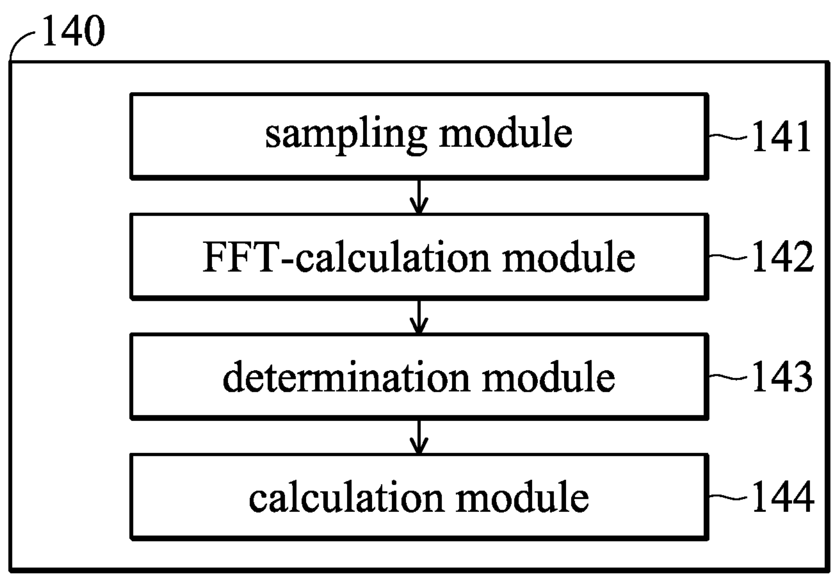
FIG. 6 is a block diagram of the control unit in accordance with an embodiment of the present disclosure.

FIG. 6 is a block diagram of the control unit 140 in accordance with an embodiment of the present disclosure. As shown in FIG. 6, the control unit 140 may include a sampling module 141, a FFT (fast Fourier transform) calculation module 142, a determination module 143, and a calculation module 144. It should be noted that the block diagram shown in FIG. 6 is only for the convenience to explain the embodiments of the present disclosure, but the present disclosure is not limited to FIG. 6. The control unit 140 may also include other components. In an embodiment of the present disclosure, the sampling module 141, the FFT-calculation module 142, the determination module 143, and the calculation module 144 may be implemented by hardware or software. In addition, according to another embodiment of the present disclosure, the sampling module 141, FFT-calculation module 142, determination module 143, and calculation module 144 may also be independent from the control unit 140.

According to an embodiment of the present disclosure, when the control unit 140 of the electrical-stimulation device 100 determines whether the signal quality of the electrical-stimulation signal generated by the electrical-stimulation signal-generating circuit 120 meets a threshold criterion, the sampling module 141 may first samples the electrical-stimulation signal generated by the electrical-stimulation signal-generating circuit 120, and transmit the sampled signal to the FFT-calculation module 142 to perform an FFT calculation. More specifically, the sampling module 141 may sample the voltage signal of the electrical-stimulation signal, and the FFT-calculation module 142 may perform the FFT calculation on the sampled voltage signal. In addition, the sampling module 141 may sample the current signal of the electrical-stimulation signal, and the FFT-calculation module 142 may perform the FFT calculation on the sampled current signal. In an embodiment of the present disclosure, the sampling module 141 samples the electrical-stimulation signal in a sampling period, and the sampling period means sampling the voltage signal and the current signal for a period of time in the pulses included in each duration $T_d$, that is, sampling the electrical-stimulation signal means sampling the pulse signal. According to an embodiment of the present disclosure, the sampling module 141 may first sample the voltage signal of the electrical-stimulation signal (e.g., taking 512 points), and the sample the current signal of the electrical-stimulation signal (e.g., taking 512 points), but the present disclosure is not limited to the sampling number or sampling order.

In an embodiment of the present disclosure, the sampling module 141 may sample each pulse signal among a plurality of pulse signals. In another embodiment of the present disclosure, the sampling module 141 may sample at least one of the plurality of pulse signals. For example, the sample module 141 may only sample one pulse signal in every two pulse signals, or sample one pulse signal in every three pulse signals. In an embodiment of the present disclosure, the data of the adjacent sampled pulse signals can be applied to the unsampled pulse signals, but the present disclosure is not limited thereto. In other words, in an embodiment of the present disclosure, in one course of electrical stimulation (i.e., completing the transmission of the first target energy value or the second target energy value to the target area), the sampling module 141 can sample at least one of the pulse signals once or multiple times to obtain a corresponding tissue-impedance value or corresponding tissue-impedance values.

The determination module 143 may determine whether the signal quality of the electrical-stimulation signal after the FFT calculation meets the threshold criterion. More specifically, the determination module 143 may determine whether a first frequency of the voltage signal after the FFT calculation and a second frequency of the current signal after the FFT calculation meet a predetermined frequency, so as to determine whether the signal quality of the electrical-stimulation signal meets the threshold criterion. In other words, when the first frequency of the voltage signal after the FFT calculation and the second frequency of the current signal after the FFT calculation meet the predetermined frequency, the determination module 143 may determine that the signal quality of the electrical-stimulation signal meets the threshold criterion. When the first frequency of the voltage signal after the FFT calculation and a second frequency of the current signal after the FFT calculation do not meet the predetermined frequency, the determination module 143 may determine that the signal quality of the electrical-stimulation signal does not meet the threshold criterion. According to an embodiment of the present disclosure, the predetermined frequency may be between 1K and 1 M Hz. According to another embodiment of the present disclosure, the predetermined frequency may be between 480K and 520K Hz.

According to an embodiment of the present disclosure, when at least one of the first frequency and the second frequency does not meet the predetermined frequency in the non-electrically stimulating phase, the determination module 143 may determine whether the voltage value that corresponds to the electrical-stimulation signal is higher than or equal to a first predetermined voltage (e.g., 2 Volts). If the voltage is lower than the first predetermined voltage, the determination module 143 may increase the voltage value of the electrical-stimulation signal by a preset value, and resample the electrical-stimulation signal. If the voltage value is higher than or equal to the first predetermined voltage value, the determination module 143 may report the external control device 200 that the tissue-impedance value cannot be calculated. According to an embodiment of the present disclosure, the preset value may be a fixed value between 0.1 to 0.4V, and the first predetermined value may be a fixed value between 1 to 4V, but the present disclosure is not limited thereto. According to an embodiment of the present disclosure, an initial voltage value of the electrical-stimulation signal may be a fixed value between 0.1 to 0.4V. In this embodiment, when the first frequency or the second frequency does not meet the aforementioned predetermined frequency, the determination module 143 may first increase a value of a counter by 1, and determine whether the value of the counter is equal to a predetermined count value. When the value of the counter is equal to the predetermined count value, the determination module 143 may report the external control device 200 that the tissue-impedance value cannot be calculated. When the value of the counter is smaller than the predetermined count value, the determination module 143 may determine whether a voltage value of the electrical-stimulation signal is higher than or equal to a first predetermined voltage value. If the first frequency and the second frequency both meet the predetermined frequency once before the value of the counter reaches the predetermined count value, the counter will be reset to 0. According to an embodiment of the present disclosure, the predetermined count value may be any value between 10 and 30.

According to an embodiment of the present disclosure, in the non-electrically stimulating phase, when the first frequency or the second frequency does not meet the aforementioned predetermined frequency, the determination module 143 may determine whether an average current value corresponding to the sampled electrical-stimulation signal is higher than or equal to a predetermined current value (e.g., 2 mA). If the average current value is smaller than the predetermined current value, the determination module 143 may increase the voltage of the electrical-stimulation signal by a preset value. If the average current value is higher than or equal to the predetermined current value, the determination module 143 may then perform subsequent calculations of the electrical-stimulation signal. According to an embodiment of the present disclosure, the preset value may be a fixed value between 0.1 to 0.4V, and the first predetermined voltage value may be a fixed value between 1 to 4V, but the present disclosure is not limited thereto. According to an embodiment of the present disclosure, an initial voltage value of the electrical-stimulation signal is a fixed value between 0.1 to 0.4V.

According to an embodiment of the present disclosure, in the electrically stimulating phase, when at least one of the first frequency and the second frequency does not meet the predetermined frequency, the determination module 143 may resample the electrical-stimulation signal, and does not use the sampled electrical-stimulation signal this time. Alternatively, the external control device 200 may not use the sampled electrical-stimulation signal this time according to the determination result from the determination module 143. In this embodiment, when at least one of the first frequency and the second frequency does not meet the predetermined frequency, the determination module 143 may use the electrical-stimulation signal that previously met the threshold criterion to perform subsequent electrical-stimulation operations. Alternatively, the external control device 200 may use the electrical-stimulation signal that previously met the threshold criterion according to the determination result of the determination module 143 to perform subsequent electrical-stimulation operations.

According to an embodiment of the present disclosure, when the determination module 143 determines that the signal quality of the electrical-stimulation signal meets the threshold criterion, the calculation module 144 may calculate an impedance value (i.e., a tissue-impedance value) corresponding to the sampled electrical-stimulation signal to perform electrical stimulation on a target area. More details will be described in the following sections.

According to an embodiment of the present disclosure, when the determination module 143 determines that the signal quality of the electrical-stimulation signal meets the threshold criterion, the calculation module 144 may extract a first voltage sample point corresponding to the maximum voltage value and a second voltage sample point corresponding to the minimum voltage value in each sampling period, and the maximum voltage value and the minimum voltage value are subtracted and divided by 2 to generate an average voltage value, which can eliminate the background value. It should be noted that, as described above, the voltage-measuring circuit 132 may increase the voltage to a positive value according to an instruction from the control unit 140, so as to facilitate the processing by the control unit 140. In addition, when the determination module 143 determines that the signal quality of the electrical-stimulation signal meets the threshold criterion, the calculation module 144 may extract a first current sample point corresponding to the maximum current value and a second current sample point corresponding to the minimum current value in each sampling period, and the maximum current value and the minimum current value are subtracted and divided by 2 to generate an average current value, which can eliminate the background value. After obtaining the average voltage value and the average current value, the calculation module 144 may obtain a total impedance value according to the average voltage value and average current value, and then calculate the tissue-impedance value according to the total impedance value. There is a more detailed description below of how to calculate the tissue-impedance value based on the total-impedance value. According to another embodiment of the present disclosure, if the background value is 0, the calculation module 144 may add the maximum voltage value and the minimum voltage value, and divide the sum by 2 to generate an average voltage value. The calculation module 144 may also add the maximum current value and the minimum current value, and divide the sum by 2 to generate an average current value.

According to another embodiment of the present disclosure, when the determination module 143 determines that the signal quality of the electrical-stimulation signal meets the threshold criterion, the sampling module 141 may sample all peaks and valleys of the voltage signal of the electrical-stimulation signal. The calculation module 144 may generate an average voltage value according to the values of all voltage sample points. For example, the calculation module 144 may average the peaks and valleys included in the 512 sampling points of the voltage signal extracted from the voltage signal in each sampling period to generate the average voltage value. In addition, the sampling module 141 may sample all peaks and valleys of the current signal of the electrical-stimulation signal. The calculation module 144 may generate an average current value according to the values of all current sample points. For example, the calculation module 144 may average the peaks and valleys in the 512 sample points extracted from the current signal in each sampling period to generate the average current value. Then, the calculation module 144 may obtain a total impedance value according to the average voltage value and the average current value, and then calculate the tissue-impedance value according to the total impedance value. There will be a more details description below on how to calculate the tissue-impedance value based on the total impedance value.

According to an embodiment of the present disclosure, before the electrical-stimulation device 100 performs electrical stimulation on the target area, such as in the non-electrically stimulating phase, the electrical-stimulation device 100 may calculate a tissue-impedance value of the target area. According to an embodiment of the present disclosure, as the electrical-stimulation device 100 shown in FIG. 2A, the electrical-stimulation device 100 may calculate the tissue-impedance value according to the impedance value of the lead and the impedance value of the electrical-stimulation device 100 itself. According to another embodiment of the present disclosure, as the electrical-stimulation device 100 shown in FIG. 2B, the electrical-stimulation device 100 may calculate the tissue-impedance value according to the impedance value of the electrical-stimulation device 100 itself. There will be more details description below.

Figure 7:
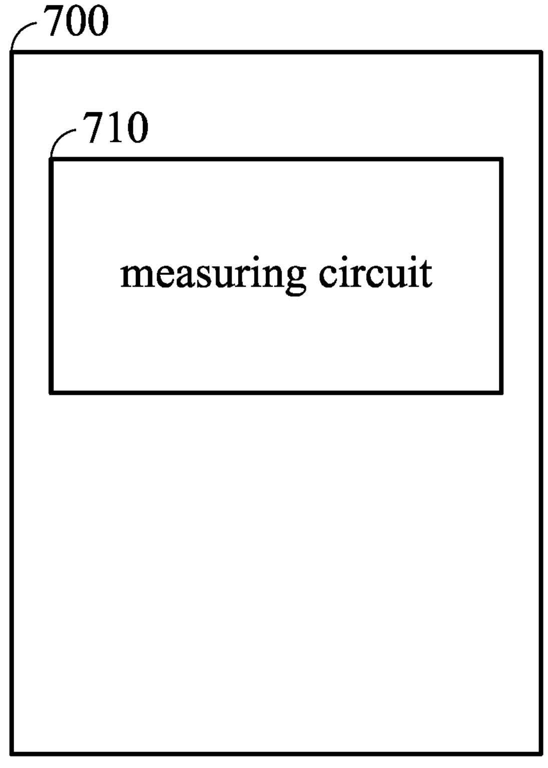
FIG. 7 is a block diagram of an impedance-compensation device in accordance with an embodiment of the present disclosure.

FIG. 7 is a block diagram of an impedance-compensation device 700 in accordance with an embodiment of the present disclosure. As shown in FIG. 7, the impedance-compensation device 700 may include a measuring circuit 710, but the present disclosure is not limited thereto. The measuring circuit 710 may be used to measure the impedance value $Z_{Inner}$ of the electrical-stimulation device 100 and the impedance value $Z_{lead}$ of the lead. According to an embodiment of the present disclosure, the impedance-compensation device 700 (or the measuring circuit 710) may also include the associated circuit structure shown in FIG. 4.

According to an embodiment of the present disclosure, when the measuring circuit 710 is to measure the electrical-stimulation device 100 as shown in FIG. 2A, the measuring circuit 710 first provides a high-frequency environment, and the frequency is the same as that of the electrical-stimulation signal being used for electrical stimulation of the target area, and 500 Hz is taken as an example here. Next, the measuring circuit 710 may measure a resistance value $R_{Lead}$, a capacitance value $C_{Lead}$, and a inductance value $L_{Lead}$ of the lead, and calculate the impedance value $Z_{Lead}$ of the lead under the high-frequency signal according to at least one of the measured resistance value $R_{Lead}$, capacitance value $C_{Lead}$, and inductance value $L_{Lead}$. In addition, the measuring circuit 710 may measure a resistance value $R_{Inner}$, a capacitance value $C_{Inner}$, and an inductance value $L_{Inner}$, of the electrical-stimulation device 100, and calculate the impedance value $Z_{Inner}$, of the electrical-stimulation device 100 according to at least one of the measured resistance value $R_{Inner}$, capacitance value $C_{Inner}$, and inductance value $L_{Inner}$. In an embodiment of the present disclosure, the inductance value $L_{Inner}$, of the electrical-stimulation device 100 may not be measured. The measuring circuit 710 may write the calculated impedance value $Z_{Lead}$ of the lead and the impedance value $Z_{Inner}$ of the electrical-stimulation device 100 to firmware of the electrical-stimulation device 100.

Figure 8A:
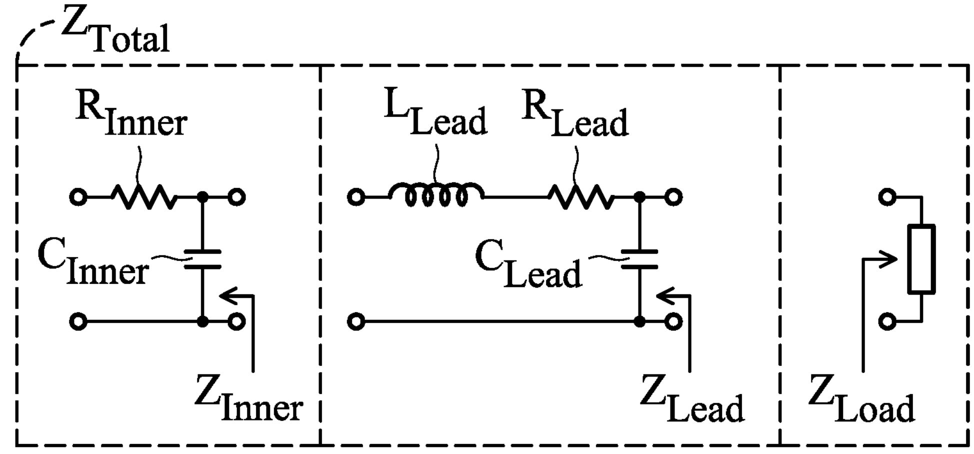
FIG. 8A is diagram of an impedance-compensation model in accordance with an embodiment of the present disclosure.

When the electrical-stimulation device 100 is to calculate the tissue-impedance value $Z_{Lead}$ of the target area, the electrical-stimulation device 100 may subtract the impedance value $Z_{Lead}$ of the lead and the impedance value $Z_{Inner}$ of the electrical-stimulation device 100 from the total impedance value $Z_{Total}$ to obtain the tissue-impedance value $Z_{Lead}$ of the target area. As shown by the impedance-compensation model in FIG. 8A, $Z_{Load}=Z_{Total}-Z_{Inner}-Z_{Lead}$, but the present disclosure is not limited thereto. In an embodiment of the present disclosure, the calculation module 144 may calculate the total impedance value $Z_{Total}$ according to the current measured by the current-measuring circuit 131 and the voltage measured by the voltage-measuring 132 (i.e., R=V/I). The calculation of the impedance value $Z_{Lead}$ of the lead and the impedance value $Z_{Inner}$ of the electrical-stimulation device 100 may refer to Z=R+j(XL−XC), where R denotes the resistance; XL denotes the inductive reactance; and XC denotes the capacitive reactance. Since the aforementioned formula is well known to those skilled in the art, so it will not be repeated here.

Figure 8B:
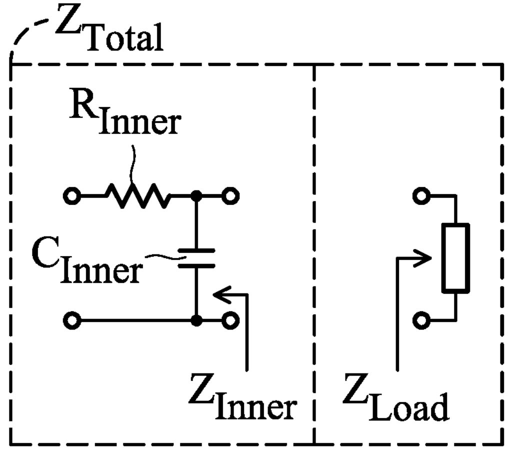
FIG. 8B is diagram of an impedance-compensation model in accordance with another embodiment of the present disclosure.

According to another embodiment of the present disclosure, when the measuring circuit 710 is to measure the electrical-stimulation device as shown in FIG. 2B, the measuring circuit 710 may first provide a high-frequency environment. The measuring circuit 710 may measure a resistance value $R_{Inner}$, a capacitance value $C_{Inner}$, and an inductance value $L_{Inner}$ of the electrical-stimulation device 100, and calculate the impedance value $Z_{Inner}$ of the electrical-stimulation device 100 according to at least one of the measured resistance value $R_{Inner}$, capacitance value $C_{Inner}$, and inductance value $L_{Inner}$. In an embodiment of the present disclosure, the inductance value $L_{Inner}$ of the electrical-stimulation device 100 may not be measured. The measuring circuit 710 may write the calculated impedance value $Z_{Lead}$ of the lead and the impedance value $Z_{Inner}$ of the electrical-stimulation device 100 to firmware of the electrical-stimulation device 100. When the electrical-stimulation device 100 is to calculate the tissue-impedance value $Z_{Load}$ of the target area, the electrical-stimulation device 100 may calculate the tissue-impedance value $Z_{Load}$ of the target area by subtracting the impedance value $Z_{Inner}$ of the electrical-stimulation device 100 from the measured total impedance value $Z_{Total}$. As shown by the impedance-compensation model in FIG. 8B, $Z_{Load}=Z_{Total}-Z_{Inner}$, but the present disclosure is not limited thereto.

According to an embodiment of the present disclosure, the measuring circuit 710 may simulate a high-frequency environment according to an electrical-stimulation frequency used by the electrical-stimulation device 100. According to an embodiment of the present disclosure, the pulse frequency range of the high-frequency environment provided by the measuring circuit 710 may be in the range of 1 KHz to 1000 KHz. According to an embodiment of the present disclosure, the pulse frequency of the high-frequency environment provided by the measuring circuit 710 is the same as that of the electrical-stimulation signal.

According to an embodiment of the present disclosure, the impedance-compensation device 700 may be disposed in the external control device 200. According to another embodiment of the present disclosure, the impedance-compensation device 700 may be disposed in the electrical-stimulation device 100. In other words, the high-frequency environment can be provided by the electrical-stimulation device 100 or the external control device 200. In addition, according to an embodiment of the prevent disclosure, the impedance-compensation device 700 may be an independent device (e.g., an impedance analyzer).

According to an embodiment of the present disclosure, the impedance-compensation device 700 can be used in the trial phase (i.e., the electrical-stimulation device 100 is an external electrical-stimulation device with a lead implanted in the body). According to an embodiment of the present disclosure, the impedance-compensation device 700 can be used in the permanent implantation phase (i.e., the electrical-stimulation device 100 is an implantable electrical-stimulation device, and it can be implanted into the human body together with the lead).

According to an embodiment of the present disclosure, the impedance-compensation device 700 can be used before production of the electrical-stimulation device 100 (e.g., laboratory or factory). In an embodiment, before the electrical-stimulation device 100 is produced, the impedance-compensation device 700 may first calculate the impedance value $Z_{Lead}$ of the lead and the impedance value $Z_{Inner}$ of the electrical-stimulation device 100, and the write the calculated impedance value $Z_{Lead}$ of the lead and the impedance value $Z_{Inner}$ of the electrical-stimulation device 100 into firmware of the electrical-stimulation device 100. In another embodiment, before the electrical-stimulation device 100 is produced, the impedance-compensation device 700 may first calculate the impedance value $Z_{Inner}$ of the electrical-stimulation device 100, and write the calculated impedance value $Z_{Inner}$ of the electrical-stimulation device 100 into the firmware of the electrical-stimulation device 100. According to an embodiment of the present disclosure, the impedance-compensation device 700 can also perform real-time compensation during the electrically stimulating phase and non-electrically stimulating phase, that is, the impedance values $Z_{Inner}$ and $Z_{Lead}$ can be measured every time an electrical-stimulation signal is sent out.

According to an embodiment of the present disclosure, after the electrical-stimulation device 100 obtains the tissue-impedance value $Z_{Load}$, the electrical-stimulation device 100 may transmit the tissue-impedance value $Z_{Load}$ to the external control device 200. The external control device 200 may determine whether the tissue-impedance value $Z_{Load}$ is within a predetermined range. During the electrically-stimulating phase, when the tissue-impedance value $Z_{Load}$ is outside the predetermined range, the external control device 200 may instruct the electrical-stimulation device 100 to stop electrical stimulation. During the electrically-stimulating phase, when the tissue-impedance value $Z_{Load}$ is within the predetermined range, the external control device 200 may instruct the electrical-stimulation device 100 to continue the electrical stimulation. According to another embodiment of the present disclosure, the electrical-stimulation device 100 may also determine by itself whether the tissue-impedance value $Z_{Load}$ is within a predetermined range. During the electrically stimulating phase, when the tissue-impedance value $Z_{Load}$ is outside the predetermined range, the electrical-stimulation device 100 may stop the electrical stimulation. During the electrically stimulating phase, when the tissue-impedance value $Z_{Load}$ is within the predetermined range, electrical-stimulation device may continue the electrical stimulation. According to an embodiment of the present disclosure, when the tissue-impedance value is outside the predetermined range, it indicates that the electrical-stimulation device 100 and the lead 210 are open-circuited. When the tissue-impedance value is within the predetermined range, it indicates that the electrical-stimulation device 100 and the lead 210 are in normal electrical connection.

According to an embodiment of the present disclosure, an upper limit and a lower limit of the predetermined range of the tissue-impedance value may be 2000 ohms and 70 ohms, respectively.

According to an embodiment of the present disclosure, after the electrical-stimulation device 100 obtains a plurality of tissue-impedance values ZLoad (e.g., three tissue-impedance values ZLoad), the calculation module 144 may calculate an average tissue-impedance value of the plurality of tissue-impedance values, and transmit the average tissue-impedance value to the external control device 200. According to an embodiment of the present disclosure, the electrical-stimulation device 100 may determine whether the average tissue-impedance value is greater than a previous average tissue-impedance value, and whether an absolute difference (i.e., regarded as "difference" for short in the following sections) between the average tissue-impedance value and the previous average tissue-impedance value is greater than a first predetermined ratio (e.g., 3%, 5%, or 10%). When the average tissue-impedance value is greater than the previous average tissue-impedance value and the absolute difference between the average tissue-impedance value and the previous tissue-impedance value is greater than the first predetermined ratio, the electrical-stimulation device 100 may calculate an average value of the average tissue-impedance value and the previous tissue-impedance value, and update the calculated average value as an output average tissue-impedance value. When the average tissue-impedance value is not greater than (i.e., equal to or smaller than) the previous average tissue-impedance value or when the absolute difference between the average tissue-impedance value and the previous average tissue-impedance value is not greater than the first predetermined ratio, the electrical-stimulation device 100 may update the average tissue-impedance value as the output average tissue-impedance value.

In addition, according to an embodiment of the present disclosure, the electrical-stimulation device 100 may determine whether the absolute difference between the output average tissue-impedance value and a previous output average tissue-impedance value (i.e., the immediately prior output average tissue-impedance value) is greater than a second predetermined ratio (e.g., 3%, 5%, or 10%). When the absolute difference between the output average tissue-impedance value and the previous output average tissue-impedance value is not greater than a second predetermined ratio, the external control device 200 may instruct the electrical-stimulation device 100 not to adjust an output current, where the output current refers to the current of the electrical-stimulation signal generated by the electrical-stimulation device 100. It should be noted that different output average tissue-impedance values may correspond to different output currents. The higher the output average tissue-impedance value is, the higher the output current is. In an embodiment, the correspondence relationship between the output average tissue-impedance value and the output current may exist in the first lookup table or a second lookup table (not show in the figure). When the absolute difference between the output average tissue-impedance value and the previous output average tissue-impedance value is greater than the second predetermined ratio, the electrical-stimulation device 100 may determine whether the output average tissue-impedance value is smaller than a predetermined impedance value (e.g., 2000 ohms). If the output average tissue-impedance output value is not smaller than (i.e., greater than or equal to) the predetermined impedance value, the electrical-stimulation device 100 may determine not to adjust the output current. If the output average tissue-impedance value is smaller than the predetermined impedance, the electrical-stimulation device 100 may adjust the output current according to the output average tissue-impedance value.

For example, after the electrical-stimulation device 100 has obtained tissue-impedance values of 290, 300, and 310 ohms for the first to third times, the electrical-stimulation device 100 may calculate the average tissue-impedance value as 300 ohms. After the electrical-stimulation device has obtained tissue-impedance values of 270, 280, and 290 ohms for the fourth to sixth times, the electrical-stimulation device may calculate the (new) average tissue-impedance value is 280 ohms. At this time, the average tissue-impedance value (i.e., 280 ohms) is smaller than the previous average tissue-impedance value (i.e., 300 ohms), and the electrical-stimulation device 100 may update 280 ohms as the output average tissue-impedance value. After the electrical-stimulation device 100 has obtained the tissue-impedance values of 340, 350, and 360 ohms for the seventh to ninth times, the electrical-stimulation device 100 may calculate the average tissue-impedance value as 350 ohms. At this time, the average tissue-impedance value (i.e., 350 ohms) is greater than the previous average tissue-impedance value (i.e., 280 ohms), and the absolute difference between the average tissue-impedance value and the previous average tissue-impedance value is greater than the first predetermined ratio (e.g., 10%). The electrical-stimulation device 100 may calculate the average value (i.e., 315 ohms) of the average tissue-impedance value (i.e., 350 ohms) and the previous tissue-impedance value (i.e., 280 ohms), and update the calculated average value as the output tissue-impedance value. Next, the electrical-stimulation device 100 may determine that the absolute difference between the output average tissue-impedance value (i.e., 315 ohms) and the previous output average tissue-impedance value (i.e., 280 ohms) is greater than the second predetermined ratio (e.g., 5%), and determine that the output average tissue-impedance value (i.e., 315 ohms) is smaller than the predetermined impedance value (e.g., 2000 ohms). Thus, the electrical-stimulation device 100 may adjust the output current according to the output average tissue-impedance value (i.e., 315 ohms).

In an embodiment of the present disclosure, the tissue-impedance value, average tissue-impedance value, output average tissue-impedance value obtained each time can exist in a buffer region of the control unit 140 or a buffer region of the storage unit 120, but the present disclosure is not limited thereto.

According to an embodiment of the present disclosure, in the electrical-stimulation phase (i.e., when the electrical-stimulation device 100 has provided electrical-stimulation treatment), in order to make the measuring circuit 130 operate smoothly, if the voltage of the electrical-stimulation signal is greater than a second predetermined voltage (e.g., 7.5V), the electrical-stimulation device 100 may generate a first predetermined number (e.g., 13) of electrical-stimulation signals, and perform voltage-lowering operation on a second predetermined number of electrical-stimulation signals among the first predetermined number of electrical-stimulation signals, where the voltage of the second predetermined number of electrical-stimulation signals is lowered to a second predetermined voltage value. That is, the subsequent calculations of the tissue-impedance values may be performed using the second number of electrical-stimulation signals on which the voltage-lower operation is performed, and the electrical-stimulation signals whose voltage is not lowered will not be used for subsequent calculations of the tissue-impedance values. The aforementioned procedure is repeated, that is, after a first predetermined number of electrical-stimulation signals are generated, a second predetermined number of electrical-stimulation signals are generated whose voltage is lowered to the second predetermined voltage value, and then a first predetermined number of electrical-stimulation signals are generated. For example, in the electrically stimulating phase, if the voltage of first N (e.g., N=10, i.e., $1^{st}$ to $10^{th}$ times) electrical-stimulation signals among the first predetermined number (e.g., 13) of electrical-stimulation signals is higher than a second predetermined voltage (e.g., 7.5V), the first N electrical-stimulation signals will not be used for subsequent calculations of the tissue-impedance values. The electrical-stimulation device 100 may perform the voltage-lowering operation (e.g., reduced to 7.5V) on the second predetermined number (e.g., $11^{th}$ to $13^{th}$) of electrical-stimulation signals, and use the specific electrical-stimulation signals after the voltage-lowering operation to perform subsequent calculations of tissue-impedance values.

In an embodiment of the present disclosure, the tissue-impedance value is used to calculate the energy value of the electrical-stimulation signal transmitted to the target area, and the energy value transmitted by the electrical-stimulation signal can be calculated using the following equation: $E=0.5*I^2*Z_{Load}*PW*rate*t$, where E denotes the energy value in joules; 0.5 is a constant; I denotes the current in amperes; PW denotes the pulse duration Td in seconds; $Z_{Load}$ denotes the tissue-impedance value in ohms; rate denotes the pulse repetition frequency of the electrical-stimulation signal in Hertz; t denotes the time for electrical stimulation in seconds.

Figure 9:
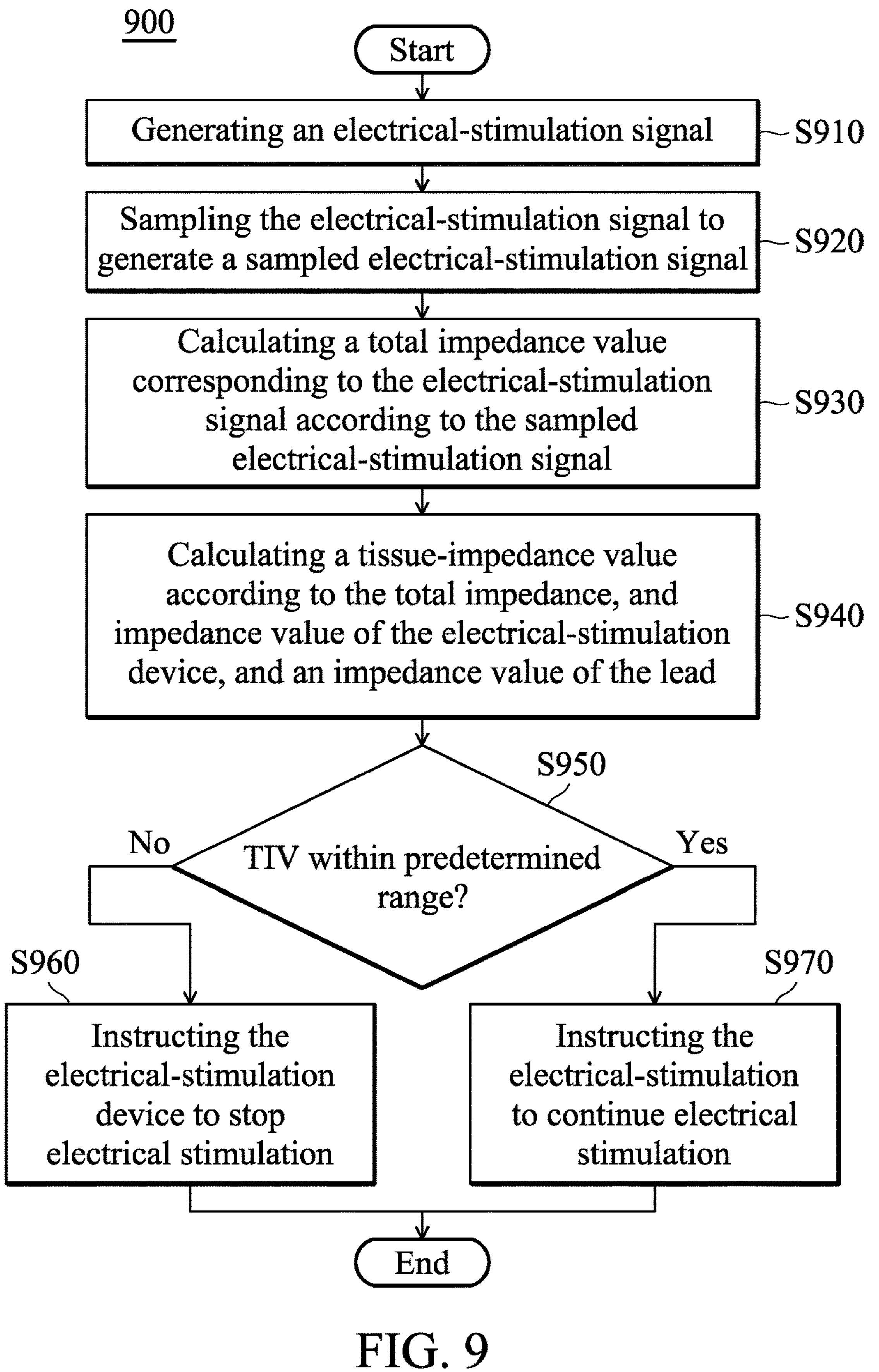
FIG. 9 is a flow chart of an impedance-monitoring method in accordance with an embodiment of the present disclosure.

FIG. 9 is a flow chart of an impedance-monitoring method in accordance with an embodiment of the present disclosure. The flow chart 900 of the impedance-monitoring method is applicable to the electrical-stimulation device 100, leads, and the external control device 200. The electrical-stimulation device 100 may store the impedance value of the electrical-stimulation device 100 and the impedance value of leads, and the impedance value of the electrical-stimulation device 100 and that of the leads are obtained at the same frequency of the electrical-stimulation signal. As shown in FIG. 9, in step S910, the electrical-stimulation device 100 generates an electrical-stimulation signal.

In step S920, the electrical-stimulation device 100 samples the electrical-stimulation signal to generate a sampled electrical-stimulation signal.

In step S930, the electrical-stimulation device 100 calculates a total impedance value corresponding to the electrical-stimulation signal according to the sampled electrical-stimulation signal.

In step S940, the electrical-stimulation device 100 calculates a tissue-impedance value according to the total impedance value, an impedance value of the electrical-stimulation device 100, and an impedance value of the lead.

In step S950, the external control device 200 receives the tissue-impedance value from the electrical-stimulation device 100, and determines whether the tissue-impedance value (TIV) is within a predetermined range.

When the tissue-impedance value is outside the predetermined range, step S960 is performed. In step S960, the external control device 200 instructs the electrical-stimulation device 100 to stop electrical stimulation.

When the tissue-impedance is within the predetermined range, step S970 is performed. In step 970, the external control device 200 instructs the electrical-stimulation device 100 to continue electrical stimulation.

Figure 10:
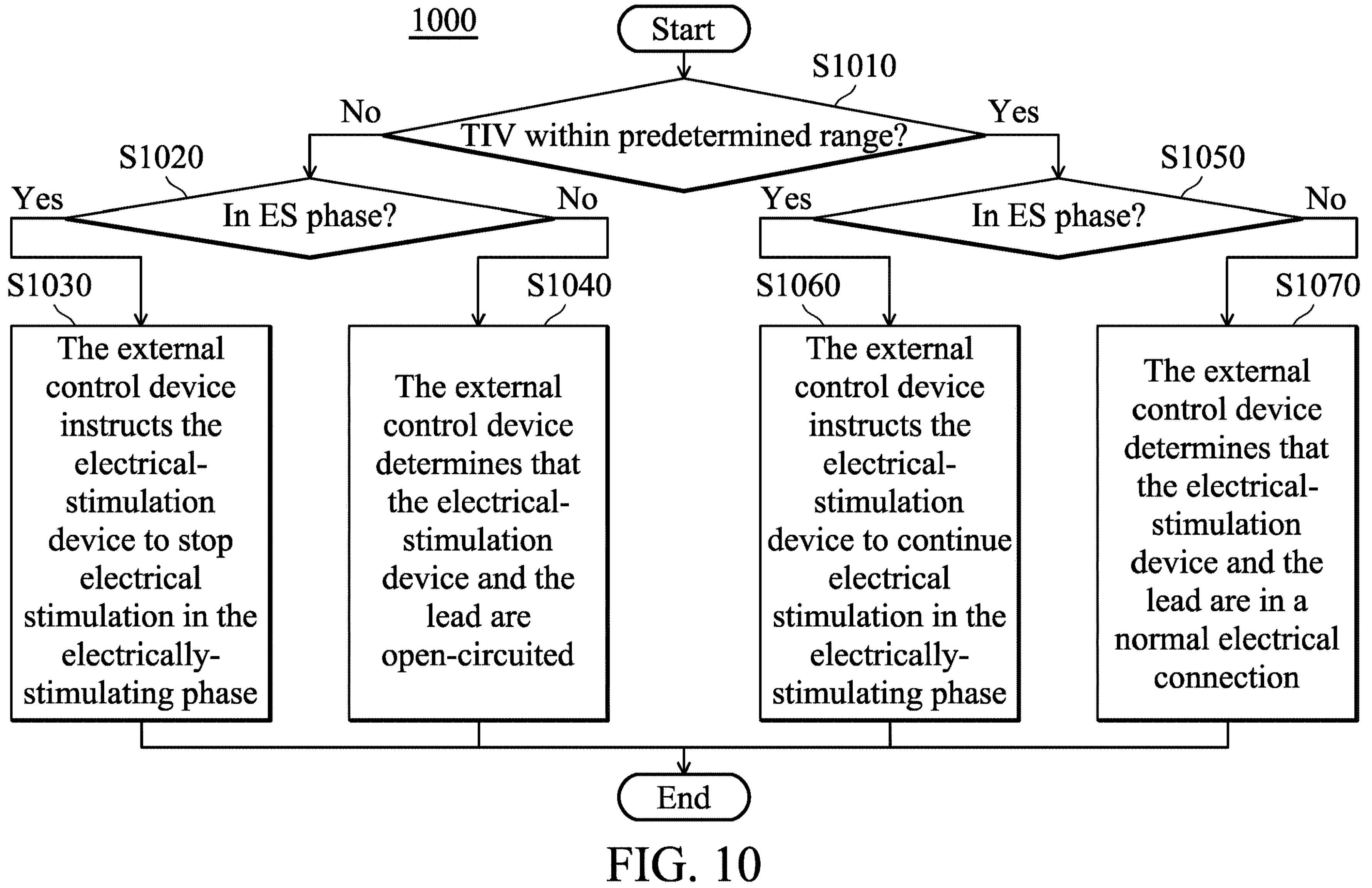
FIG. 10 is a flow chart 1000 of an impedance-monitoring method in accordance with another embodiment of the present disclosure.

FIG. 10 is a flow chart 1000 of an impedance-monitoring method in accordance with another embodiment of the present disclosure. The flow chart 1000 of the impedance-monitoring method is applicable to the electrical-stimulation device 100, leads, and the external control device 200. The electrical-stimulation device 100 may store the impedance value of the electrical-stimulation device 100 and the impedance value of leads, and the impedance value of the electrical-stimulation device 100 and that of the leads are obtained at the same frequency of the electrical-stimulation signal. As shown in FIG. 10, in step S1010, the external control device 200 determines whether the tissue-impedance value (TIV) is within a predetermined range.

When the tissue-impedance value is outside the predetermined range, step S1020 is performed. In step S1020, the external control device 200 determines whether it is in an electrically stimulating (ES) phase. When the external control device 200 is in the electrically stimulating phase, step S1030 is performed. In step S1030, the external control device 200 instructs the electrical-stimulation device 100 to stop electrical stimulation in the electrically stimulating phase. When the external control device 200 is in a non-electrically stimulating phase, step S1040 is performed. In step S1040, the external control device 200 determines that the electrical-stimulation device 100 and the lead are open-circuited.

When the tissue-impedance value is within the predetermined range, step S1050 is performed. In step S1050, the external control device 200 determines whether it is in an electrically stimulating phase. When the external control device 200 is in the electrically stimulating phase, step S1060 is performed. In step S1060, the external control device 200 instructs the electrical-stimulation device 100 to continue electrical stimulation in the electrically stimulating phase. When the external control device 200 is in a non-electrically stimulating phase, step S1070 is performed. In step S1070, the external control device 200 determines that the electrical-stimulation device 100 and the lead are in a normal electrical connection.

Figure 11:
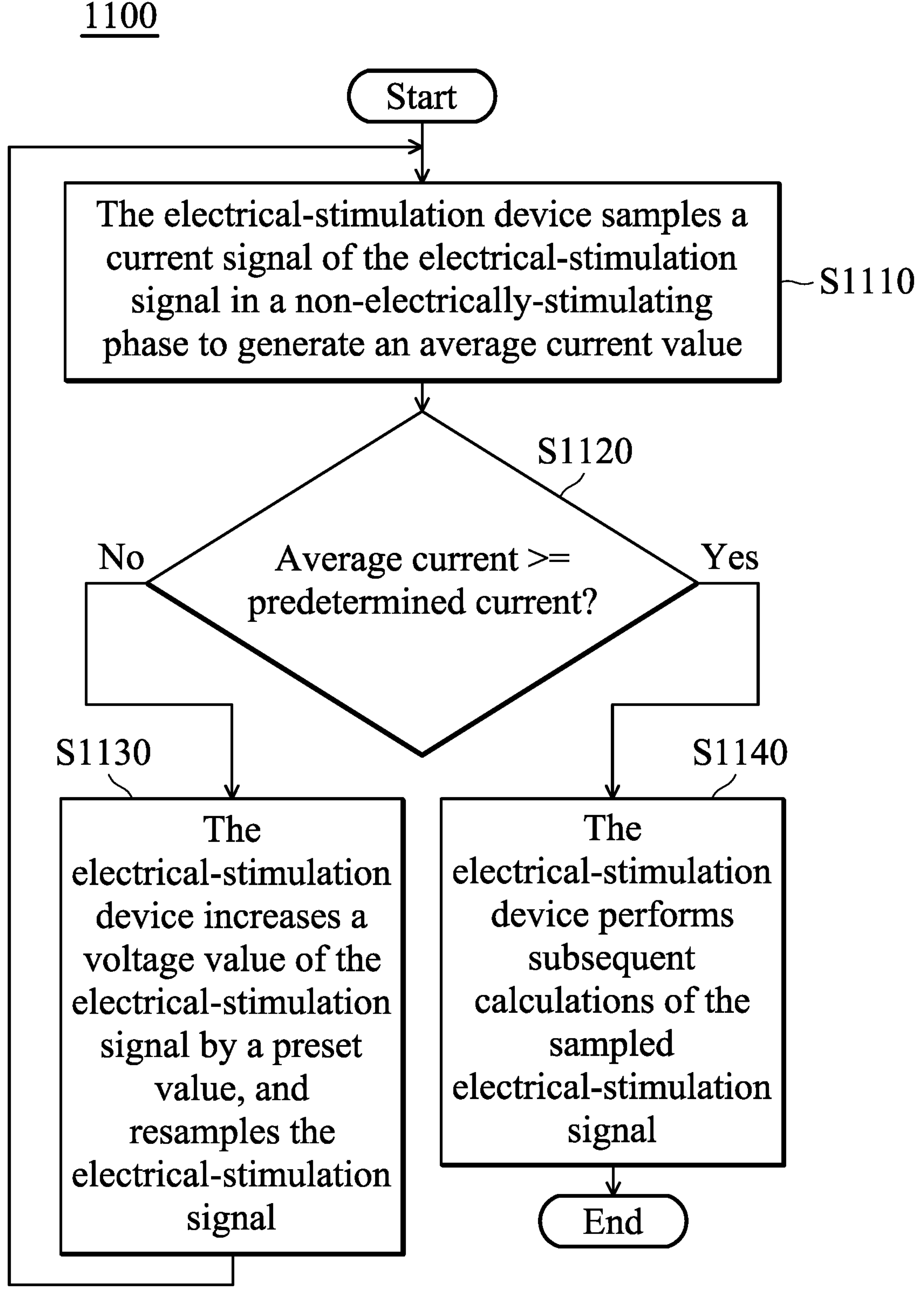
FIG. 11 is a flow chart 1100 of a method for processing an electrical-stimulation signal in accordance with an embodiment of the present disclosure.

FIG. 11 is a flow chart 1100 of a method for processing an electrical-stimulation signal in accordance with an embodiment of the present disclosure. The flow chart 1100 of the method for processing the electrical-stimulation signal is applicable to the electrical-stimulation device 100. As shown in FIG. 11, in step S1110, the electrical-stimulation device 100 samples a current signal of the electrical-stimulation signal in a non-electrically stimulating phase to generate an average current value.

In step S1120, the electrical-stimulation device 100 determines whether the average current value is greater than or equal to a predetermined current value.

If the average current value is smaller than the predetermined current value, step S1130 is performed. In step S1130, the electrical-stimulation device 100 increases a voltage value of the electrical-stimulation signal by a preset value, and resamples the electrical-stimulation signal.

If the average current value is greater than or equal to the predetermined current value, step S1140 is performed. In step S1140, the electrical-stimulation device 100 performs subsequent calculations of the sampled electrical-stimulation signal.

Figure 12:
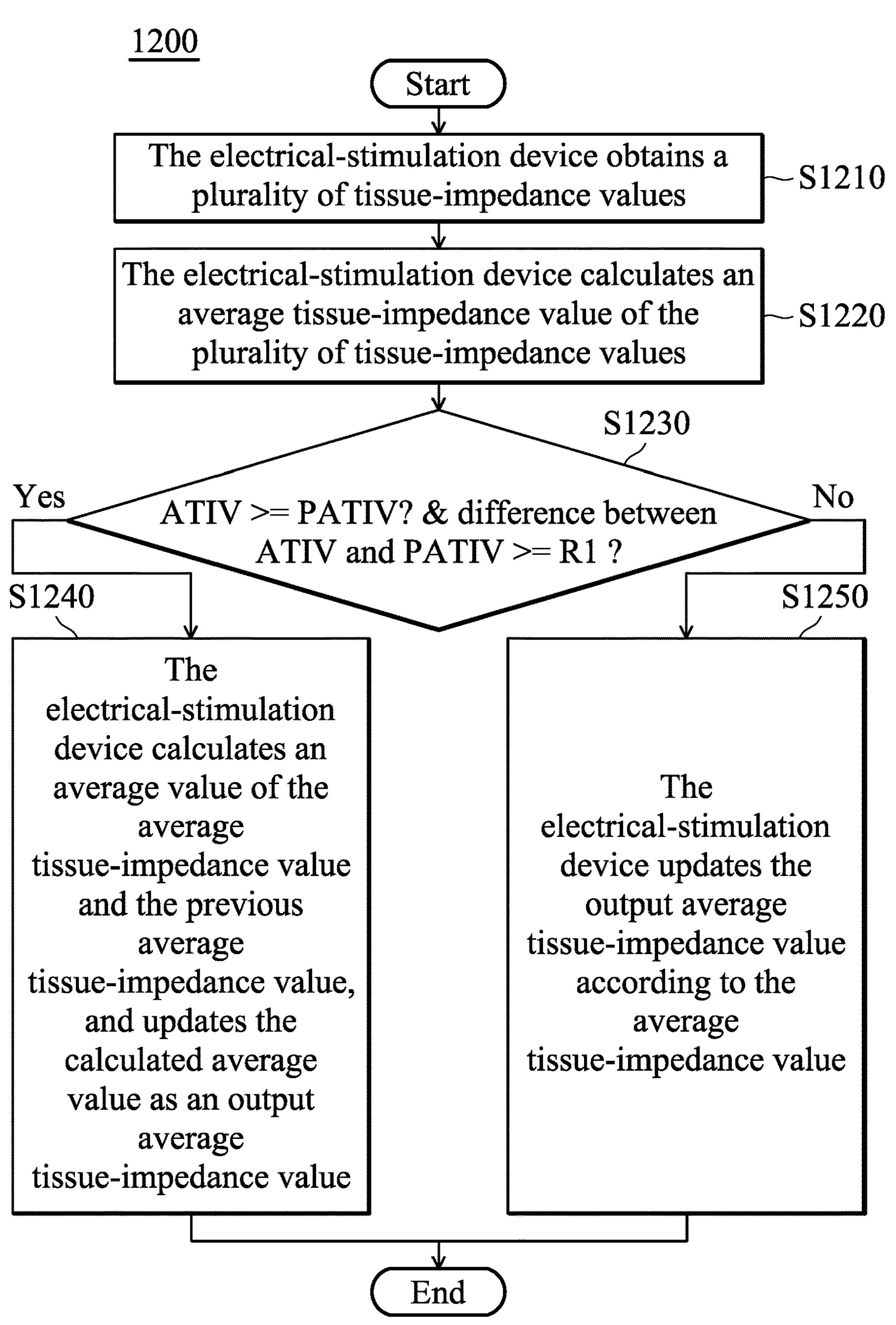
FIG. 12 is a flow chart 1200 of a method for updating an output average tissue-impedance value in accordance with an embodiment of the present disclosure.

FIG. 12 is a flow chart 1200 of a method for updating an output average tissue-impedance value in accordance with an embodiment of the present disclosure. The flow chart 1200 of the method for updating the output average tissue-impedance value is applicable to the electrical-stimulation device 100. As shown in FIG. 12, in step S1210, the electrical-stimulation device 100 obtains a plurality of tissue-impedance values.

In step S1220, the electrical-stimulation device 100 calculates an average tissue-impedance value of the plurality of tissue-impedance values.

In step S1230, the electrical-stimulation device 100 determines whether the average tissue-impedance value (ATIV) is greater than a previous average tissue-impedance value (PATIV), and whether a difference between the average tissue-impedance value and the previous average tissue-impedance value is greater than a first predetermined ratio (R1).

When the average tissue-impedance value is greater than the previous average tissue-impedance value and the difference is greater than the first predetermined ratio, step S1240 is performed. In step S1240, the electrical-stimulation device 100 calculates an average value of the average tissue-impedance value and the previous average tissue-impedance value, and updates the calculated average value as an output average tissue-impedance value.

When the average tissue-impedance value is not greater than the previous average tissue-impedance value or the difference is not greater than the first predetermined ratio, step S1250 is performed. In step S1250, the electrical-stimulation device 100 updates the output average tissue-impedance value according to the average tissue-impedance value.

Figure 13:
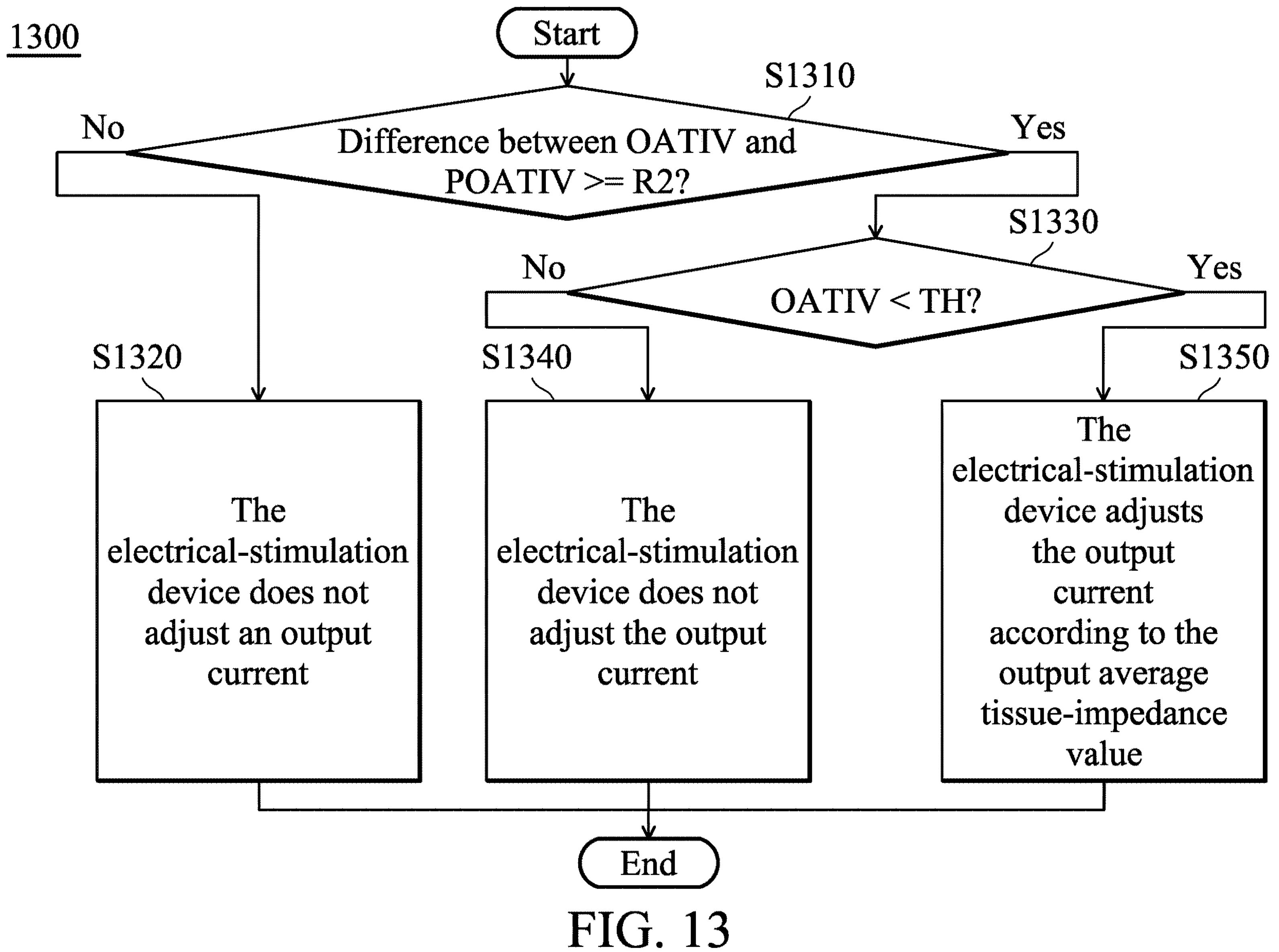
FIG. 13 is a flow chart 1300 of a method for adjusting the output current in accordance with an embodiment of the present disclosure.

FIG. 13 is a flow chart 1300 of a method for adjusting the output current in accordance with an embodiment of the present disclosure. The flow chart 1300 of the method for adjusting the output current is applicable to the electrical-stimulation device 100. As shown in FIG. 13, in step S1310, the electrical-stimulation device 100 determines whether the difference between the output average tissue-impedance value (OATIV) and the previous output average tissue-impedance value (POATIV) is greater than a second predetermined ratio (R2).

When the difference is not greater than the second predetermined ratio, step S1320 is performed. In step S1320, the electrical-stimulation device 100 does not adjust an output current of the electrical-stimulation device 100.

When the difference is greater than the second predetermined ratio, step S1330 is performed. In step S1330, the electrical-stimulation device 100 determines whether the output average tissue-impedance value (OATIV) is smaller than a predetermined impedance value TH.

When the output average tissue-impedance value is not smaller than the predetermined impedance value, step S1340 is performed. In step S1340, the electrical-stimulation device 100 does not adjust the output current.

When the output average tissue-impedance value is smaller than the predetermined impedance value, step S1350 is performed. In step S1350, the electrical-stimulation device 100 adjusts the output current according to the output average tissue-impedance value.

According to an embodiment of the present disclosure, a computer-readable storage medium can store one or more instructions, and cooperate with the electrical-stimulation device 100 and the external control device 200 for providing electrical stimulation. When the computer-readable storage medium stores one or more instructions to be executed by the electrical-stimulation device 100 and the external control device 200, the electrical-stimulation device 100 and the external control device 200 can perform the plurality of steps included in the impedance-monitoring method.

According to the impedance-monitoring method proposed in the present disclosure, it will be possible to determine whether the calculated tissue-impedance value is within a predetermined range during electrical stimulation. Therefore, it can be prevented that the calculated tissue-impedance value is too large or too small, causing discomfort to the user when performing electrical stimulation. In addition, conventionally, when the electrical-stimulation device is implanted into the human body, the human tissue may coat the electrical-stimulation device and the lead, or the tissue impedance may change due to changes in the posture of the human body as time increases. Therefore, according to the impedance-monitoring method proposed in the present disclosure, it is possible to continuously monitor the changes of tissue impedance in a relatively real-time manner during electrical stimulation.

Ordinal terms used in the claims, such as "first," "second," "third," etc., are only for convenience of explanation, and do not imply any precedence relation between one another.

The steps of the methods and algorithms provided in the present disclosure may be directly applied to a hardware and a software module or the combination thereof by executing a processor. A software module (including executing instructions and related data) and other data may be stored in a data memory, such as random access memory (RAM), flash memory, read-only memory (ROM), erasable programmable read only memory (EPROM), electrically erasable programmable read only memory (EEPROM), registers, hard drives, portable drives, CD-ROM, DVD, or any other computer-readable storage media format in the art. For example, a storage media may be coupled to a machine device, such as a computer/processor (denoted by "processor" in the present disclosure, for the convenience of explanation). The processor may read information (such as codes) from and write information to a storage media. A storage media may integrate a processor. An application-specific integrated circuit (ASIC) includes the processor and the storage media. A user apparatus includes an ASIC. In other words, the processor and the storage media are included in the user apparatus without directly connecting to the user apparatus. Besides, in some embodiments, any product suitable for computer programs includes a readable storage media, wherein the storage media includes codes related to one or more disclosed embodiments. In some embodiments, the computer program product may include packaging materials.

The above paragraphs are described with multiple aspects. Obviously, the teachings of the specification may be performed in multiple ways. Any specific structure or function disclosed in examples is only a representative situation. According to the teachings of the specification, it should be noted by those skilled in the art that any aspect disclosed may be performed individually, or that more than two aspects could be combined and performed.

While the invention has been described by way of example and in terms of the preferred embodiments, it should be understood that the invention is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An impedance-monitoring method, applied to an electrical-stimulation device and a lead, wherein the electrical-stimulation device stores an impedance value of the electrical-stimulation device itself and an impedance value of the lead, the method comprising:

utilizing the electrical-stimulation device to generate an electrical-stimulation signal, and to perform electrical stimulation on a target area using the electrical-stimulation signal;

utilizing the electrical-stimulation device to sample the electrical-stimulation signal to calculate a total impedance value corresponding to the electrical-stimulation signal;

utilizing the electrical-stimulation device to calculate a tissue-impedance value according to the total impedance value, the impedance value of the electrical-stimulation device itself, and the impedance value of the lead, wherein the tissue-impedance value is used to calculate an energy value of the electrical-stimulation signal transmitted to the target area; and utilizing the electrical-stimulation device to stop electrical stimulation of the target area when the energy generated by the electrical-stimulation signal has reached a target energy value.

2. The impedance-monitoring method as claimed in claim 1, wherein in the step of utilizing the electrical-stimulation device to sample the electrical-stimulation signal to calculate a total impedance value corresponding to the electrical-stimulation signal, the electrical-stimulation signal comprises a plurality of pulse signals, and the electrical-stimulation device samples at least one of the plurality of pulse signals to calculate the total impedance value corresponding to at least one of the plurality of pulse signals.

3. The impedance-monitoring method as claimed in claim 1, wherein the tissue-impedance value is the total impedance value minus the impedance value of the electrical-stimulation device itself and the impedance value of the lead.

4. The impedance-monitoring method as claimed in claim 1, wherein the impedance value of the electrical-stimulation device itself and the impedance value of the lead are measured in an environment with the same frequency as the electrical-stimulation signal.

5. The impedance-monitoring method as claimed in claim 1, further comprising:

determining whether the tissue-impedance value is within a predetermined range;

when the tissue-impedance value is outside the predetermined range in an electrically stimulating phase, instructing the electrical-stimulation device to stop electrical stimulation in the electrically stimulating phase; and when the tissue-impedance value is within the predetermined range in the electrically stimulating phase, instructing the electrical-stimulation device to continue the electrical stimulation in the electrically stimulating phase, wherein an upper limit and a lower limit of the predetermined range are 2000 ohms and 70 ohms, respectively.

6. The impedance-monitoring method as claimed in claim 5, wherein when the tissue-impedance value is outside the predetermined range in a non-electrically stimulating phase, the electrical-stimulation device and the lead are open-circuited; and wherein when the tissue-impedance value is within the predetermined range, the electrical-stimulation device and the lead are in a normal electrical connection.

7. The impedance-monitoring method as claimed in claim 1, further comprising:

sampling a current signal of the electrical-stimulation signal in a non-electrically stimulating phase to generate an average current value;

determining whether the average current value is greater than or equal to a predetermined current value; and in response to the average current value being smaller than the predetermined current value, increasing a voltage value of the electrical-stimulation signal by a preset value, and resampling the electrical-stimulation signal.

8. The impedance-monitoring method as claimed in claim 1, wherein a frequency of the electrical-stimulation signal is between 1K and 1M Hz.

9. The impedance-monitoring method as claimed in claim 1, further comprising:

utilizing the electrical-stimulation device to obtain a plurality of tissue-impedance values;

utilizing the electrical-stimulation device to calculate an average tissue-impedance value of the plurality of tissue-impedance values;

utilizing the electrical-stimulation device to determine whether the average tissue-impedance value is greater than a previous average tissue-impedance value, and whether a first difference between the average tissue-impedance value and the previous tissue-impedance value is greater than a first predetermined ratio;

when the average tissue-impedance value is greater than the previous average tissue-impedance value and the first difference is greater than the first predetermined ratio, averaging the average tissue-impedance value and the previous average tissue-impedance value to generate an average value, and updating the average value as an output average tissue-impedance value; and when the tissue-impedance value is not greater than the previous average tissue-impedance value or the first difference is not greater than the first predetermined ratio, updating the output average tissue-impedance value according to the average tissue-impedance value.

10. The impedance-monitoring method as claimed in claim 9, further comprising:

utilizing the electrical-stimulation device to determine whether a second difference between the output tissue-impedance value and a previous output tissue-impedance value is greater than a second predetermined ratio;

when the second difference is not greater than the second predetermined ratio, not adjusting an output current of the electrical-stimulation device;

when the second difference is greater than the second predetermined ratio, determining whether the output average tissue-impedance value is smaller than a predetermined impedance;

when the output average tissue-impedance value is not greater than the predetermined impedance, not adjusting the output current of the electrical-stimulation device; and when the output average tissue-impedance value is smaller than the predetermined impedance, adjusting the output current according to the average tissue-impedance value.

11. The impedance-monitoring method as claimed in claim 1, wherein the step of utilizing the electrical-stimulation device to sample the electrical-stimulation signal to calculate the total impedance value corresponding to the electrical-stimulation signal further comprises:

utilizing the electrical-stimulation device to generate a first predetermined number of electrical-stimulation signals, and to perform a voltage-lowering operation on a second predetermined number of electrical-stimulation signals among the first predetermined number of electrical-stimulation signals, and to sample the voltage-lowered electrical-stimulation signals to calculate the total impedance value corresponding to the electrical-stimulation signal.

12. An electrical-stimulation system, comprising:

an external control device;

a lead; and an electrical-stimulation device, electrically connected to the external device and the lead, wherein the electrical-stimulation device comprises:

a storage unit, storing an impedance value of the electrical-stimulation device itself and an impedance value of the lead;

an electrical-stimulation-signal generating circuit, generating an electrical-stimulation signal and performing electrical stimulation on a target area using the electrical-stimulation signal;

a sampling module, sampling the electrical-stimulation signal; and a calculation module, calculating a total impedance value corresponding to the electrical-stimulation signal, and calculating a tissue-impedance value according to the total impedance value, the impedance value of the electrical-stimulation device itself, and the impedance value of the lead, wherein the tissue-impedance value is used to calculate an energy value of the electrical-stimulation signal transmitted to the target area;

wherein the electrical-stimulation-signal generating circuit stops electrical stimulation of the target area when the energy generated by the electrical-stimulation signal has reached the target energy value.

13. The electrical-stimulation system as claimed in claim 12, wherein the electrical-stimulation signal comprises a plurality of pulse signals, and the electrical-stimulation device samples at least one of the plurality of pulse signals to calculate the total impedance value corresponding to at least one of the plurality of pulse signals.

14. The electrical-stimulation system as claimed in claim 12, wherein the tissue-impedance value is the total impedance value minus the impedance value of the electrical-stimulation device itself and the impedance value of the lead.

15. The electrical-stimulation system as claimed in claim 12, wherein the impedance value of the electrical-stimulation device itself and the impedance value of the lead are measured in an environment with the same frequency as the electrical-stimulation signal.

16. The electrical-stimulation system as claimed in claim 12, wherein the electrical-stimulation device transmits the tissue-impedance value to the external control device, and the electrical-stimulation device or the external control device determines whether the tissue-impedance value is within a predetermined range.

17. The electrical-stimulation system as claimed in claim 16, wherein when the tissue-impedance value is outside the predetermined range in an electrically stimulating phase, the electrical-stimulation device or the external control device instructs the electrical-stimulation device to stop electrical stimulation in the electrically stimulating phase, wherein when the tissue-impedance value is within the predetermined range in the electrically stimulating phase, the electrical-stimulation device or the external control device instructs the electrical-stimulation device to continue the electrical stimulation in the electrically stimulating phase, wherein an upper limit and a lower limit of the predetermined range are 2000 ohms and 70 ohms, respectively.

18. The electrical-stimulation system as claimed in claim 16, wherein when the tissue-impedance value is outside the predetermined range in a non-electrically stimulating phase, the electrical-stimulation device and the lead are open-circuited; and wherein when the tissue-impedance value is within the predetermined range, the electrical-stimulation device and the lead are in a normal electrical connection, wherein an upper limit and a lower limit of the predetermined range are 2000 ohms and 70 ohms, respectively.

19. The electrical-stimulation system as claimed in claim 12, wherein the sampling module samples a current signal of the electrical-stimulation signal in a non-electrically stimulating phase to generate an average current value, and determines whether the average current value is greater than or equal to a predetermined current value, wherein in response to the average current value being smaller than the predetermined current value, the calculation module increases a voltage value of the electrical-stimulation signal by a preset value, and resamples the electrical-stimulation signal.

20. The electrical-stimulation system as claimed in claim 12, wherein a frequency of the electrical-stimulation signal is between 1K and 1M Hz.

21. The electrical-stimulation system as claimed in claim 12, wherein the electrical-stimulation device obtains a plurality of tissue-impedance values, and calculates an average tissue-impedance value of the plurality of tissue-impedance values, wherein the electrical-stimulation device determines whether the average tissue-impedance value is greater than a previous average tissue-impedance value, and whether a first difference between the average tissue-impedance value and the previous tissue-impedance value is greater than a first predetermined ratio, wherein when the average tissue-impedance value is greater than the previous average tissue-impedance value and the first difference is greater than the first predetermined ratio, the electrical-stimulation device averages the average tissue-impedance value and the previous average tissue-impedance value to generate an average value, and updates the average value as an output average tissue-impedance value, wherein when the tissue-impedance value is not greater than the previous average tissue-impedance value or the first difference is not greater than the first predetermined ratio, the electrical-stimulation device updates the output average tissue-impedance value according to the average tissue-impedance value.

22. The electrical-stimulation system as claimed in claim 21, wherein the electrical-stimulation device determines whether a second difference between the output tissue-impedance value and a previous output tissue-impedance value is greater than a second predetermined ratio, wherein when the second difference is not greater than the second predetermined ratio, the electrical-stimulation device does not adjust an output current of the electrical-stimulation device, wherein when the second difference is greater than the second predetermined ratio, the electrical-stimulation device determines whether the output average tissue-impedance value is smaller than a predetermined impedance, wherein when the output average tissue-impedance value is not greater than the predetermined impedance, the electrical-stimulation device does not adjust the output current of the electrical-stimulation device, wherein when the output average tissue-impedance value is smaller than the predetermined impedance, the electrical-stimulation device adjusts the output current according to the average tissue-impedance value.

23. The electrical-stimulation system as claimed in claim 12, wherein the electrical-stimulation device generates a first predetermined number of electrical-stimulation signals, and performs a voltage-lowering operation on a second predetermined number of electrical-stimulation signals among the first predetermined number of electrical-stimulation signals, and samples the voltage-lowered electrical-stimulation signals to calculate the total impedance value corresponding to the electrical-stimulation signal.

24. A computer-readable storage medium, storing one or more instructions and cooperating with an external control device and an electrical-stimulation device, wherein the electrical-stimulation device stores an impedance value of the electrical-stimulation device itself and an impedance value of the lead, when the one or more instructions are executed by the external control device or the electrical-stimulation device, the external control device or the electrical-stimulation device performs the following operations:

utilizing the electrical-stimulation device to generate an electrical-stimulation signal, and to perform electrical stimulation on a target area using the electrical-stimulation signal;

utilizing the electrical-stimulation device to sample the electrical-stimulation signal to calculate a total impedance value corresponding to the electrical-stimulation signal; and utilizing the electrical-stimulation device to calculate a tissue-impedance value according to the total impedance value, the impedance value of the electrical-stimulation device itself, and the impedance value of the lead, wherein the tissue-impedance value is used to calculate an energy value of the electrical-stimulation signal transmitted to the target area; and utilizing the electrical-stimulation device to stop electrical stimulation of the target area when the energy generated by the electrical-stimulation signal has reached the target energy value.

25. The computer-readable storage medium as claimed in claim 24, wherein the tissue-impedance value is the total impedance value minus the impedance value of the electrical-stimulation device itself and the impedance value of the lead.

26. The computer-readable storage medium as claimed in claim 24, wherein the impedance value of the electrical-stimulation device itself and the impedance value of the lead are measured in an environment with the same frequency as the electrical-stimulation signal.

27. The computer-readable storage medium as claimed in claim 26, wherein in the step of utilizing the electrical-stimulation device to sample the electrical-stimulation signal to calculate a total impedance value corresponding to the electrical-stimulation signal, the electrical-stimulation signal comprises a plurality of pulse signals, and the electrical-stimulation device samples at least one of the plurality of pulse signals to calculate the total impedance value corresponding to at least one of the plurality of pulse signals.

28. The computer-readable storage medium as claimed in claim 24, wherein the operations further comprise:

determining whether the tissue-impedance value is within a predetermined range, wherein an upper limit and a lower limit of the predetermined range are 2000 ohms and 70 ohms, respectively.

29. The computer-readable storage medium as claimed in claim 28, wherein the operations further comprise:

when the tissue-impedance value is outside the predetermined range in an electrically stimulating phase, instructing the electrical-stimulation device to stop electrical stimulation in the electrically stimulating phase; and when the tissue-impedance value is within the predetermined range in the electrically stimulating phase, instructing the electrical-stimulation device to continue the electrical stimulation in the electrically stimulating phase.

30. The computer-readable storage medium as claimed in claim 29, wherein the operations further comprise:

utilizing the electrical-stimulation device to obtain a plurality of tissue-impedance values;

utilizing the electrical-stimulation device to calculate an average tissue-impedance value of the plurality of tissue-impedance values;

utilizing the electrical-stimulation device to determine whether the average tissue-impedance value is greater than a previous average tissue-impedance value, and whether a first difference between the average tissue-impedance value and the previous tissue-impedance value is greater than a first predetermined ratio;

when the average tissue-impedance value is greater than the previous average tissue-impedance value and the first difference is greater than the first predetermined ratio, averaging the average tissue-impedance value and the previous average tissue-impedance value to generate an average value, and updating the average value to an output average tissue-impedance value; and when the tissue-impedance value is not greater than the previous average tissue-impedance value or the first difference is not greater than the first predetermined ratio, updating the output average tissue-impedance value according to the average tissue-impedance value.

31. The computer-readable storage medium as claimed in claim 30, wherein the operations further comprise:

utilizing the electrical-stimulation device to determine whether a second difference between the output tissue-impedance value and a previous output tissue-impedance value is greater than a second predetermined ratio;

when the second difference is not greater than the second predetermined ratio, not adjusting an output current of the electrical-stimulation device;

when the second difference is greater than the second predetermined ratio, determining whether the output average tissue-impedance value is smaller than a predetermined impedance;

when the output average tissue-impedance value is not greater than the predetermined impedance, not adjusting the output current of the electrical-stimulation device; and when the output average tissue-impedance value is smaller than the predetermined impedance, adjusting the output current according to the average tissue-impedance value.

32. The computer-readable storage medium as claimed in claim 28, wherein when the tissue-impedance value is outside the predetermined range in a non-electrically stimulating phase, the electrical-stimulation device and the lead are open-circuited; and wherein when the tissue-impedance value is within the predetermined range, the electrical-stimulation device and the lead are in a normal electrical connection.

33. The computer-readable storage medium as claimed in claim 24, wherein the operations further comprise:

sampling a current signal of the electrical-stimulation signal in a non-electrically stimulating phase to generate an average current value;

determining whether the average current value is greater than or equal to a predetermined current value; and in response to the average current value being smaller than the predetermined current value, increasing a voltage value of the electrical-stimulation signal by a preset value, and resampling the electrical-stimulation signal.

34. The computer-readable storage medium as claimed in claim 24, wherein a frequency of the electrical-stimulation signal is between 1K and 1M Hz.

35. The computer-readable storage medium as claimed in claim 24, wherein the step of utilizing the electrical-stimulation device to sample the electrical-stimulation signal to calculate a total impedance value corresponding to the electrical-stimulation signal further comprises:

utilizing the electrical-stimulation device to generate a first predetermined number of electrical-stimulation signals, and to perform a voltage-lowering operation on a second predetermined number of electrical-stimulation signals among the first predetermined number of electrical-stimulation signals, and to sample the voltage-lowered electrical-stimulation signals to calculate the total impedance value corresponding to the electrical-stimulation signal.

* * * * *